US006808498B2

(12) United States Patent
Laroya et al.

(10) Patent No.: US 6,808,498 B2
(45) Date of Patent: Oct. 26, 2004

(54) PLACING A GUIDE MEMBER INTO A HEART CHAMBER THROUGH A CORONARY VESSEL AND DELIVERING DEVICES FOR PLACING THE CORONARY VESSEL IN COMMUNICATION WITH THE HEART CHAMBER

(75) Inventors: Gilbert S. Laroya, Santa Clara, CA (US); A. Adam Sharkawy, Redwood City, CA (US); Mark J. Foley, Menlo Park, CA (US)

(73) Assignee: Ventrica, Inc., Fremont, CA (US)

(*) Notice: Subject to any disclaimer, the term of this patent is extended or adjusted under 35 U.S.C. 154(b) by 0 days.

(21) Appl. No.: 09/170,793

(22) Filed: Oct. 13, 1998

(65) Prior Publication Data

US 2002/0077566 A1 Jun. 20, 2002

Related U.S. Application Data

(63) Continuation-in-part of application No. 09/023,492, filed on Feb. 13, 1998.

(51) Int. Cl.[7] ............................................. A61B 5/00
(52) U.S. Cl. ..................................... 600/585; 604/528
(58) Field of Search ................................ 600/434, 435, 600/585; 604/95, 158, 164, 523, 528

(56) References Cited

U.S. PATENT DOCUMENTS

| 2,127,903 A | 8/1938 | Bowen |
| 2,453,056 A | 11/1948 | Zack |
| 3,042,021 A | 7/1962 | Read |
| 3,316,914 A | 5/1967 | Collito |
| 3,540,451 A | 11/1970 | Zeman |
| 3,774,615 A | 11/1973 | Lim et al. |
| 4,300,244 A | 11/1981 | Brokos |
| 4,400,833 A | 8/1983 | Kurland |

(List continued on next page.)

FOREIGN PATENT DOCUMENTS

| GB | 2316322 | 2/1998 |
| SU | 1754128 | 3/1989 |
| WO | WO 82/01644 | 5/1982 |
| WO | WO 84/02266 | 6/1984 |
| WO | WO 88/06865 | 9/1988 |
| WO | WO 90/15582 | 12/1990 |
| WO | WO 94/21197 | 9/1994 |
| WO | WO 96/22745 | 8/1996 |
| WO | WO 97/13463 | 1/1997 |
| WO | WO 97/13471 | 4/1997 |
| WO | WO 97/27893 | 8/1997 |
| WO | WO 97/27897 | 8/1997 |

(List continued on next page.)

OTHER PUBLICATIONS

Ahmed SS et al., Silent left coronary artery–cameral fistula: Probable cause of myocardial ischemia, Amer. Heart Journal, 1982;104(4):869–872.

Arani D et al., Coronary artery fistulas emptying into left heart chambers, Amer. Heart J., 1977;438–443.

Black IW et al., Multiple coronary artery–left ventricular fistulae: clinical, angiographic, and pathologic findings, Catheterization Cardiovascular Diagnosis, 1991;23:133–135.

(List continued on next page.)

*Primary Examiner*—Max Hindenburg
(74) *Attorney, Agent, or Firm*—Hoekendijk & Lynch, LLP

(57) ABSTRACT

A guide member positioned through a coronary vessel and the wall of the heart provides access to a heart chamber. A first end of the guide member is passed through the coronary vessel and the heart wall into the heart chamber, and then is passed back out of the heart chamber. The end of the guide member may then be used to deliver devices into the heart chamber to carry out various medical procedures. A conduit delivery system is coupled to the end of the guide member and is delivered into the heart chamber and then used to place a conduit in the heart wall to communicate the coronary vessel with the heart chamber.

31 Claims, 18 Drawing Sheets

U.S. PATENT DOCUMENTS

| | | |
|---|---|---|
| 4,523,592 A | 6/1985 | Daniel |
| 4,728,328 A | 3/1988 | Hughes |
| 4,769,029 A | 9/1988 | Patel |
| 4,769,031 A | 9/1988 | McGough et al. |
| 4,955,856 A | 9/1990 | Philips |
| 4,955,899 A | 9/1990 | Della Corna et al. |
| 4,976,691 A * | 12/1990 | Sahota ............... 600/585 |
| 4,995,857 A | 2/1991 | Arnold |
| 5,054,484 A | 10/1991 | Hebeler, Jr. |
| 5,078,735 A | 1/1992 | Mobin-Uddin |
| 5,131,406 A * | 7/1992 | Kaltenbach ........... 600/585 |
| 5,250,058 A | 10/1993 | Miller et al. |
| 5,254,113 A | 10/1993 | Wilk |
| 5,287,861 A | 2/1994 | Wilk |
| 5,318,527 A * | 6/1994 | Hyde et al. ........... 600/585 |
| 5,327,913 A | 7/1994 | Taheri |
| 5,383,892 A | 1/1995 | Cardon et al. |
| 5,409,019 A | 4/1995 | Wilk |
| 5,429,144 A | 7/1995 | Wilk |
| 5,443,497 A | 8/1995 | Venbrux |
| 5,456,714 A | 10/1995 | Owen |
| 5,466,242 A | 11/1995 | Mori |
| 5,503,635 A | 4/1996 | Sauer et al. |
| 5,591,226 A | 1/1997 | Trerotola et al. |
| 5,655,548 A | 8/1997 | Nelson et al. |
| 5,662,124 A | 9/1997 | Wilk |
| 5,695,504 A | 12/1997 | Gifford, III et al. |
| 5,697,943 A | 12/1997 | Sauer et al. |
| 5,715,818 A * | 2/1998 | Swartz et al. ......... 600/585 |
| 5,755,682 A | 5/1998 | Knudson et al. |
| 5,755,778 A | 5/1998 | Kleshinski |
| 5,758,663 A | 6/1998 | Wilk et al. |
| 5,810,836 A | 9/1998 | Hussein et al. |
| 5,814,005 A | 9/1998 | Barra et al. |
| 5,817,113 A | 10/1998 | Gifford, III et al. |
| 5,824,042 A | 10/1998 | Lombardi et al. |
| 5,824,071 A | 10/1998 | Nelson et al. |
| 5,830,222 A | 11/1998 | Makower |
| 5,830,224 A | 11/1998 | Cohn et al. |
| 5,836,316 A | 11/1998 | Plaia et al. |
| 5,843,088 A | 12/1998 | Barra et al. |
| 5,843,165 A | 12/1998 | Plaia et al. |
| 5,855,597 A | 1/1999 | Jayaraman |
| 5,871,536 A | 2/1999 | Lazarus |
| 5,875,782 A | 3/1999 | Ferrari et al. |
| 5,879,321 A | 3/1999 | Hill |
| 5,888,201 A | 3/1999 | Stinson et al. |
| 5,888,247 A | 3/1999 | Benetti |
| 5,893,886 A | 4/1999 | Zegdi et al. |
| 5,895,407 A | 4/1999 | Jayaraman |
| 5,897,587 A | 4/1999 | Martakos et al. |
| 5,897,589 A | 4/1999 | Cottenceau et al. |
| 5,904,697 A | 5/1999 | Gifford, III et al. |
| 5,908,028 A | 6/1999 | Wilk |
| 5,908,029 A | 6/1999 | Knudson et al. |
| 5,910,168 A | 6/1999 | Myers et al. |
| 5,911,753 A | 6/1999 | Schmitt |
| 5,913,894 A | 6/1999 | Schmitt |
| 5,916,226 A | 6/1999 | Tozzi |
| 5,916,264 A | 6/1999 | Von Oepen et al. |
| 5,925,033 A | 7/1999 | Aita et al. |
| 5,941,893 A | 8/1999 | Saadat |
| 5,941,908 A | 8/1999 | Goldsteen et al. |
| 5,944,019 A | 8/1999 | Knudson et al. |
| 5,971,993 A | 10/1999 | Hussein et al. |
| 5,976,178 A | 11/1999 | Goldsteen et al. |
| 5,980,567 A | 11/1999 | Jordan |
| 5,984,956 A | 11/1999 | Tweden et al. |
| 5,989,276 A | 11/1999 | Houser et al. |
| 5,989,287 A | 11/1999 | Yang et al. |
| 5,993,489 A | 11/1999 | Lewis et al. |
| 6,001,124 A | 12/1999 | Bachinski |
| 6,029,672 A | 2/2000 | Vanney et al. |
| 6,053,942 A | 4/2000 | Eno et al. |
| 6,076,529 A | 6/2000 | Vanney et al. |
| 6,092,526 A | 7/2000 | LaFontaine et al. |
| 6,093,166 A | 7/2000 | Knudson et al. |

FOREIGN PATENT DOCUMENTS

| | | |
|---|---|---|
| WO | WO 97/27898 | 8/1997 |
| WO | WO 97/32545 | 9/1997 |
| WO | WO 98/06356 | 2/1998 |
| WO | WO 98/08456 | 3/1998 |
| WO | WO 98/16161 | 4/1998 |
| WO | WO 98/16174 | 4/1998 |
| WO | WO 98/19608 | 5/1998 |
| WO | WO 98/19614 | 5/1998 |
| WO | WO 98/19630 | 5/1998 |
| WO | WO 98/19631 | 5/1998 |
| WO | WO 98/19634 | 5/1998 |
| WO | WO 98/19635 | 5/1998 |
| WO | WO 98/19636 | 5/1998 |
| WO | WO 98/23241 | 6/1998 |
| WO | WO 98/38939 | 9/1998 |
| WO | WO 98/38941 | 9/1998 |
| WO | WO 98/38942 | 9/1998 |
| WO | WO 98/38947 | 9/1998 |
| WO | WO 98/46115 | 10/1998 |
| WO | WO 98/46119 | 10/1998 |
| WO | WO 98/49964 | 11/1998 |
| WO | WO 98/55027 | 12/1998 |
| WO | WO 98/57590 | 12/1998 |
| WO | WO 98/57591 | 12/1998 |
| WO | WO 98/57592 | 12/1998 |
| WO | WO 99/17683 | 4/1999 |
| WO | WO 99/18887 | 4/1999 |
| WO | WO 99/21490 | 5/1999 |
| WO | WO 99/22658 | 5/1999 |
| WO | WO 99/25273 | 5/1999 |
| WO | WO 99/36000 | 7/1999 |
| WO | WO 99/36001 | 7/1999 |
| WO | WO 99/37349 | 7/1999 |
| WO | WO 99/38441 | 8/1999 |
| WO | WO 99/38454 | 8/1999 |
| WO | WO 99/38459 | 8/1999 |
| WO | WO 99/40868 | 8/1999 |
| WO | WO 99/48545 | 9/1999 |
| WO | WO 99/49793 | 10/1999 |
| WO | WO 99/49910 | 10/1999 |
| WO | WO 99/51162 | 10/1999 |
| WO | WO 99/53863 | 10/1999 |
| WO | WO 99/60941 | 12/1999 |
| WO | WO 99/62430 | 12/1999 |
| WO | WO 00/12029 | 3/2000 |
| WO | WO 00/15146 | 3/2000 |
| WO | WO 00/15147 | 3/2000 |
| WO | WO 00/15148 | 3/2000 |
| WO | WO 00/15149 | 3/2000 |
| WO | WO 00/15275 | 3/2000 |
| WO | WO 00/24449 | 5/2000 |

OTHER PUBLICATIONS

Cha SD et al., Silent coronary artery–left ventricular fistula: A disorder of the Thebesian system?, Angiology, 1978; 169–173.

Cha SD, Coronary Artery to Left Ventricular Fistula, Cath. Cardiovas. Diagnosis, 1991;24:150–152.

Cheng TO et al., Traumatic aneurysm of left anterior descending coronary artery with fistulous opening into left ventricle and left ventricular aneurysm after stab wound of chest, Amer. J. Cardio., 1973;31:384–390.

Chia BL et al, Coronary artery–left ventricular fistula, Cardiology, 1981;68:167–179.

Cooley DA et al., Surgical considerations of coronary arterial fistula, Amer. J. Cardio., 1962;X(4):467–474.

Elian, D, Left Coronary Artery to Left Ventricular Fistula, Cath. Cardiovas. Diagnosis, 1998;43:490–493.

Flynn AE et al., Does systolic subepicardial perfusion come from retrograde subendocardial flow? American Physiological Society, 1992;262:H1759–H1769.

Galioto FM et al., Right coronary artery to left ventricle fistula, Amer. Heart J., 1971;82(1):93–97.

Goldman A et al., Experimental methods for producing a collateral ciruclation to the heart directly from the left ventricle, J. Thoracic. Surg., 1956;31(3):364–374.

Haravon A. et al., Congenital coronary artery to left ventricle fistula with angina pectoris, NY State J. Med.,. 1972;2196–2200.

Hufnagel CA et al., Surgical correction of aortic insufficiency. Surgery, 1954;35 (5):637–683.

Koyama, T et al., Non–uniform oxygen supply to the left ventricular myocardium by systolic perfusion of coronary artery, Japanese J of Physiology, 1979, 29, 267–274.

Massimo C et al., Myocardial revascularization by a new method of carrying blood directly from the left ventricular cavity into the coronary circulation, J. Thorac. Surg., 1957, 34(2):257–264.

Matsumae M et al., An experimental study of new sutureless intraluminal graft with an elastic ring that can attach itself to the vessel wall. J. Vasc. Surg., 1988;8:38–44.

McLellan BA et al. Myocardial infarction due to multiple coronary–ventricular fistulas. Catheterization and Cardiovascular Diagnosis, 1989;16:247–249.

McNamara J et al., Congenital coronary artery fistula, Surgery, 1969;65(1):59–69.

Midell AI et al., Surgical closure of left coronary artery–left ventricular fistula, J. Thor. Cardiovasc. Surg., 1977; 199–203.

Munro I et al., The possibility of myocardial revascularization by creation of a left ventriculocoronary artery fistula, J Thor. Cardiovas. Surg., 1969;58(1):25–32.

Nishida H et al., Flow study of surgical coronary artery fistula as an alternative to sequential bypass, Cardiovasc. Surg., 1995;3(4):375–380.

O'Connor WN et al., Ventriculocoronary connections in hypoplastic left hearts: An autopsy microscopic study, Circulation, 1982;66(5):1078–1086.

Okuda Y et al., Right coronary artery to left ventricle fistula, Jap. Heart J., 1973;14(2):184–191.

Pifarré R et al., Myocardial revascularization from the left ventricle: A physiologic impossibility, Surgical Forum, 1968;19:157–159.

Reddy K. et al., Multiple coronary arteriosystemic fistulas, Amer. J. Cardio., 1974;33:304–306.

Ryan C et al., Fistula from coronary arteries to left ventricle after myocardial infarction, British Heart J., 1977;39:1147–1149.

Sastri DM, et al., Coronary artery left ventricular fistula, Chest, 1975;68(5):735–736.

Sheikhzadeh A et al., Generalized coronary Arterio–systemic (left ventricular) fistula. Jpn. Heart J., 1986;27 (4):533–544.

Stevens JH et al., Port–access coronary artery bypass grafting: A proposed surgical method, J. Thoracic Cardiovas. Surg., 1996;111(3):567–573.

Vineberg A, Coronary vascular anastomoses by internal mammary artery implantation, Can. M.A.J., 1958; 78:871–879.

Wolff PF et al., Fistules coronaro–ventriculaires gauches, Mal Coéur., 1981;74(11):1353–1357.

U.S. Priority application Ser. No. 08/878,804 for PCT WO 98/57591.

U.S. Priority application Ser. No. 09/088,496 for PCT WO 98/57592.

* cited by examiner

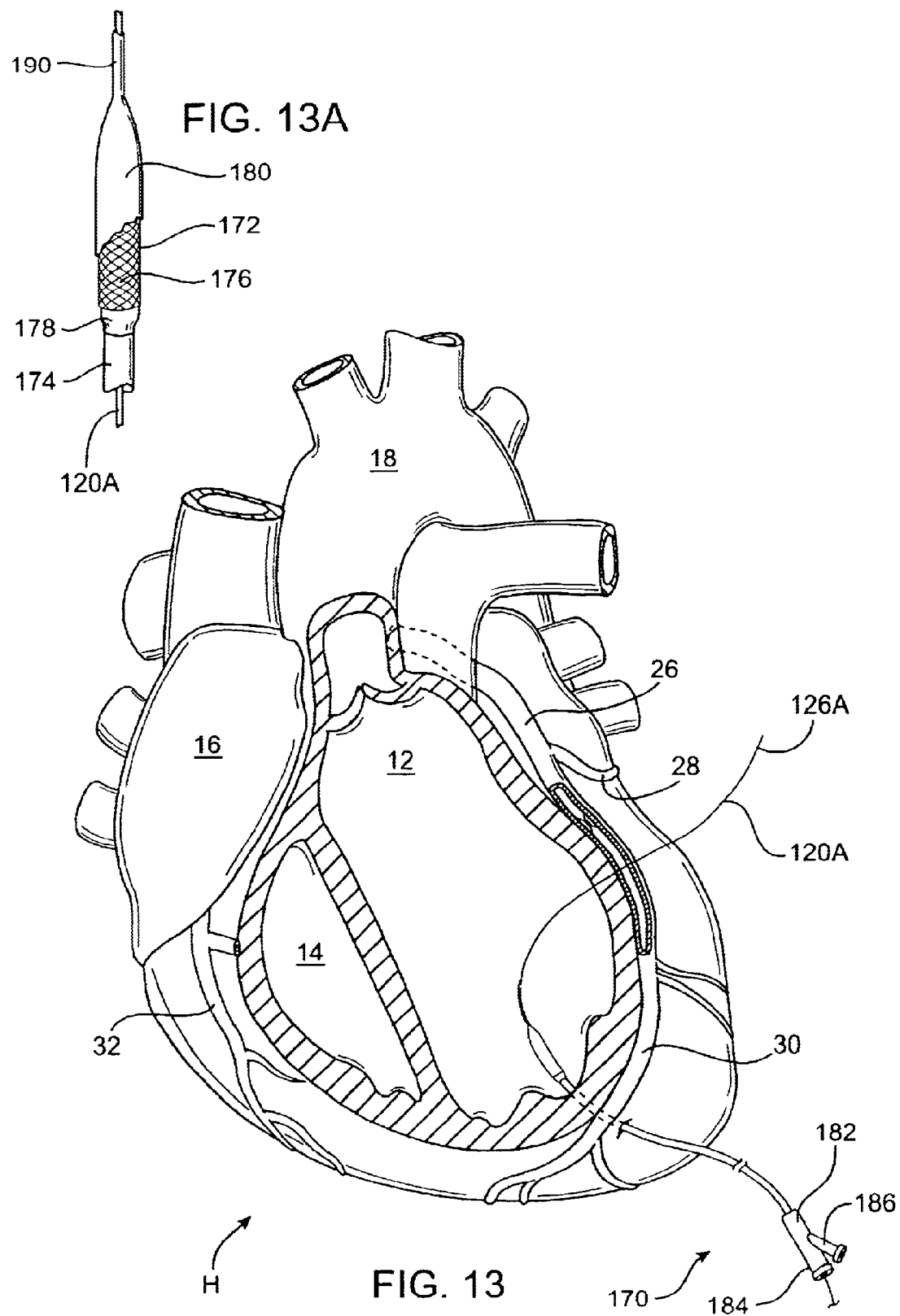

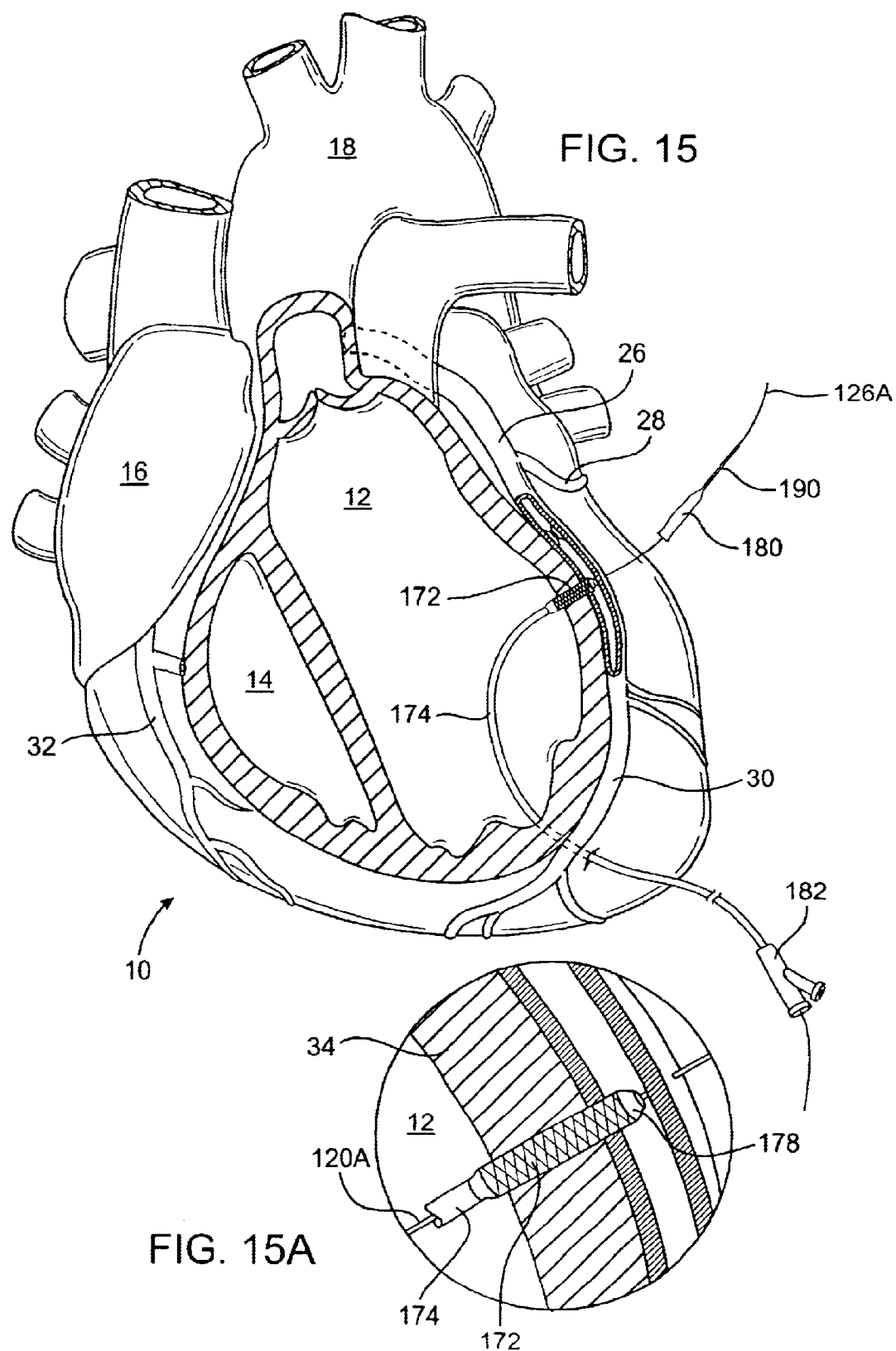

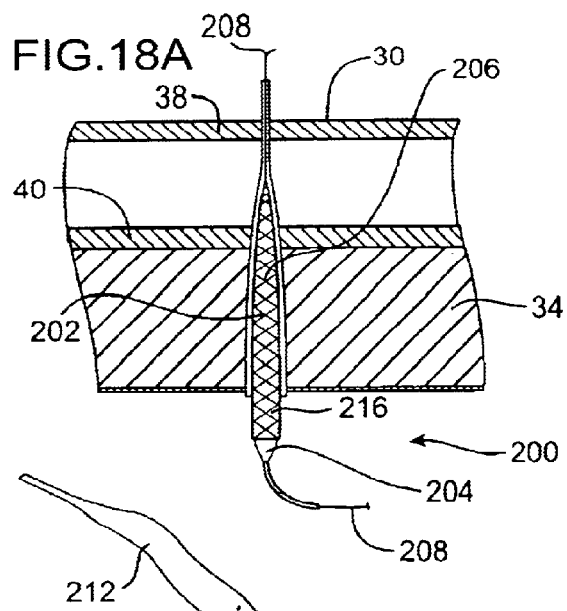
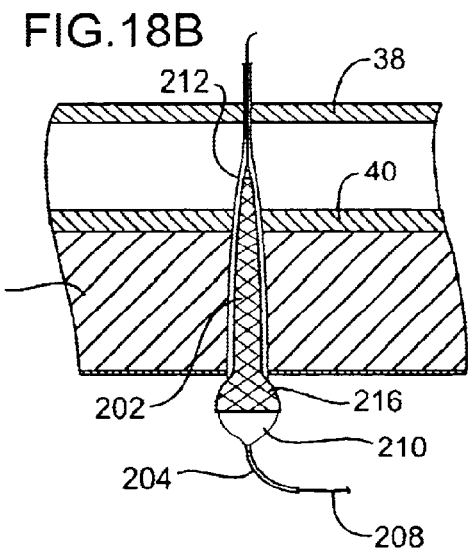
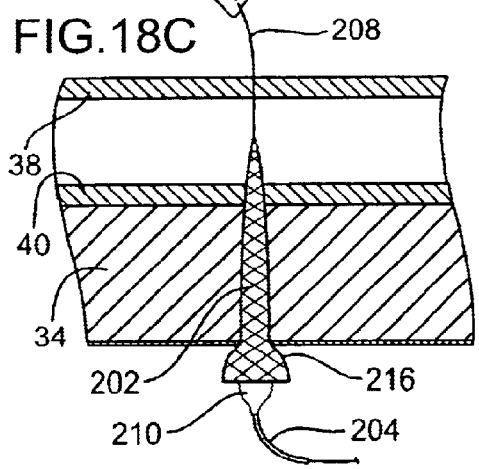
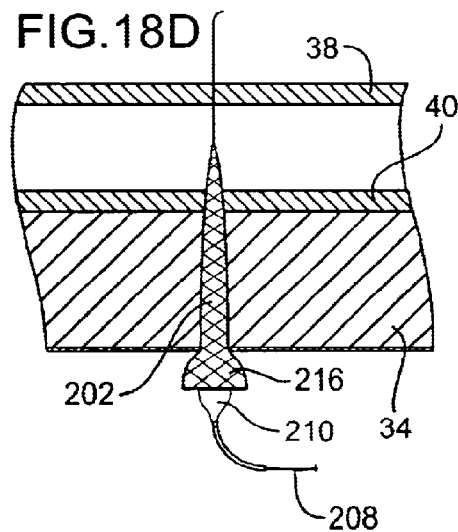
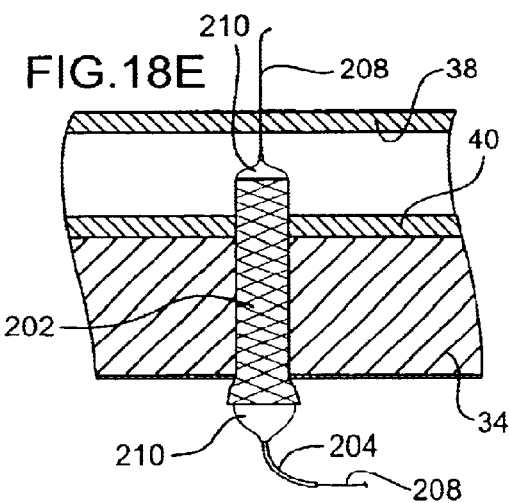
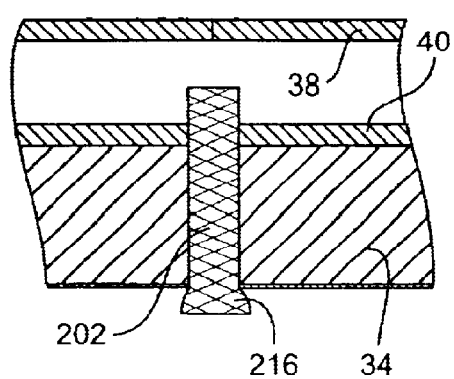

PLACING A GUIDE MEMBER INTO A HEART CHAMBER THROUGH A CORONARY VESSEL AND DELIVERING DEVICES FOR PLACING THE CORONARY VESSEL IN COMMUNICATION WITH THE HEART CHAMBER

CROSS-REFERENCE TO RELATED APPLICATIONS

This application is a continuation-in-part of application Ser. No. 09/023,492, filed Feb. 13, 1998, and entitled "Methods and Devices Providing Transmyocardial Blood Flow to the Arterial Vascular System of the Heart," now abandoned the entire subject matter of which application is incorporated herein by reference.

BACKGROUND OF THE INVENTION

1. Field of the Invention

The invention relates to treating heart disease, and more particularly systems, devices and methods for reestablishing or improving blood flow to the myocardium.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue the search for new and improved treatments.

Coronary artery disease is currently treated by interventional procedures such as percutaneous transluminal coronary angioplasty (PTCA), atherectomy and intracoronary stenting, as well as surgical procedures including coronary artery bypass grafting (CABG). The goal of these procedures is to reestablish or improve blood flow through occluded (or partially occluded) coronary arteries, which is accomplished, for example, by enlarging the blood flow lumen of the artery or by forming a bypass that allows blood to circumvent the occlusion. What procedure(s) is used typically depends on the severity and location of the blockages. When successful, these procedures restore blood flow to myocardial tissue that had not been sufficiently perfused due to the occlusion.

Technological and procedural advances have improved the results obtained by the medical procedures now used to treat heart disease, and in particular coronary artery disease. There is, however, still much room for improvement. For that reason there remains a need in the art for new and improved systems, devices and methods for treating heart disease such as arteriosclerosis.

SUMMARY OF THE INVENTION

In a first embodiment, the invention provides a system and method for placing a guide member through a coronary vessel and the wall of patient's heart into a heart chamber. The guide member may then be used to deliver devices into the heart chamber to carry out various medical procedures. In one preferred system constructed according to this embodiment, an introducer is configured for placement through the wall of a patient's heart so as to extend into a heart chamber. The introducer receives a guide member sized and configured to be passed through the introducer, the coronary vessel and the heart wall into the heart chamber. In another preferred system, the introducer is constructed to position the guide member at a desired location within the heart chamber that allows the guide member to be removed from the chamber.

In one preferred method carried out according to this embodiment, a first end of a guide member is passed through a coronary vessel and the wall of the heart into a heart chamber. A second end of the guide member is maintained outside the heart chamber, and the first end of the guide member is then passed back out of the heart chamber. One of the ends of the guide member may be used to introduce medical devices into the heart chamber.

In a second embodiment, the invention provides a system and method for placing a conduit in the wall of a patient's heart to communicate a coronary vessel with a heart chamber. One preferred system constructed according to this embodiment includes an introducer configured for placement through the wall of a patient's heart into a heart chamber, a guide member sized and configured to be positioned in the introducer and placed through the heart wall into the heart chamber, and a conduit. The conduit is configured for placement in the heart wall to communicate the heart chamber with a coronary vessel.

One preferred method carried out according to this embodiment comprises positioning a guide member that extends through a coronary vessel and the heart wall into a heart chamber. The guide member is used to deliver a conduit into the heart chamber and the conduit is positioned in the heart wall to place the coronary vessel in communication with the heart chamber, thereby establishing a blood flow path between the heart chamber and the vessel.

BRIEF DESCRIPTION OF THE DRAWINGS

The invention will be better understood from the following detailed description of preferred embodiments thereof, taken in conjunction with the accompanying drawing figures, wherein:

FIG. 13 is a perspective view illustrating another conduit placement system for placing a conduit in a heart wall, the system being used with a guide member positioned in the heart chamber as shown in FIG. 8;

FIG. 13A is an enlarged view of a portion of the system of FIG. 13;

FIGS. 14, 15 and 16 are perspective views sequentially illustrating using the conduit placement system shown in FIG. 13 to place a conduit in the heart wall; FIGS. 14A, 15A and 16A are enlarged sectional views of the system shown in FIGS. 14, 15 and 16, respectively;

FIGS. 18A–18F are elevation views, in section, sequentially illustrating yet another conduit and conduit placement system, wherein FIG. 18F shows the conduit positioned in the heart wall.

DETAILED DESCRIPTION OF PREFERRED EMBODIMENTS

The present invention provides methods and devices for placing a guide member through a coronary vessel and a heart wall so that the guide member extends into a heart chamber containing blood, as well as methods and devices for placing a conduit in the heart wall to establish a blood flow path between a coronary vessel and a heart chamber. The guide member is preferably introduced through the coronary vessel which allows precise control of the guide member. It should be noted that, as used herein, coronary vessel refers to any vessel in the vascular structure of the heart, including but not limited to the arterial vascular structure including coronary arteries, septal perforators. As such, it will be understood that the LAD 30 illustrated in the Figures is but one example of a possible vessel which may receive a guide member or be placed in communication with a heart chamber.

Similarly, in the preferred embodiments the LAD 30 is placed in communication with a heart chamber that contains blood, which, in the illustrated embodiments, is the left ventricle 12. It will be understood, however, that the invention may be used to place a conduit in communication with any source of blood (arterial or venous), for example, another heart chamber such as the left atrium, or the aorta, pulmonary veins, etc.

Figure 1:
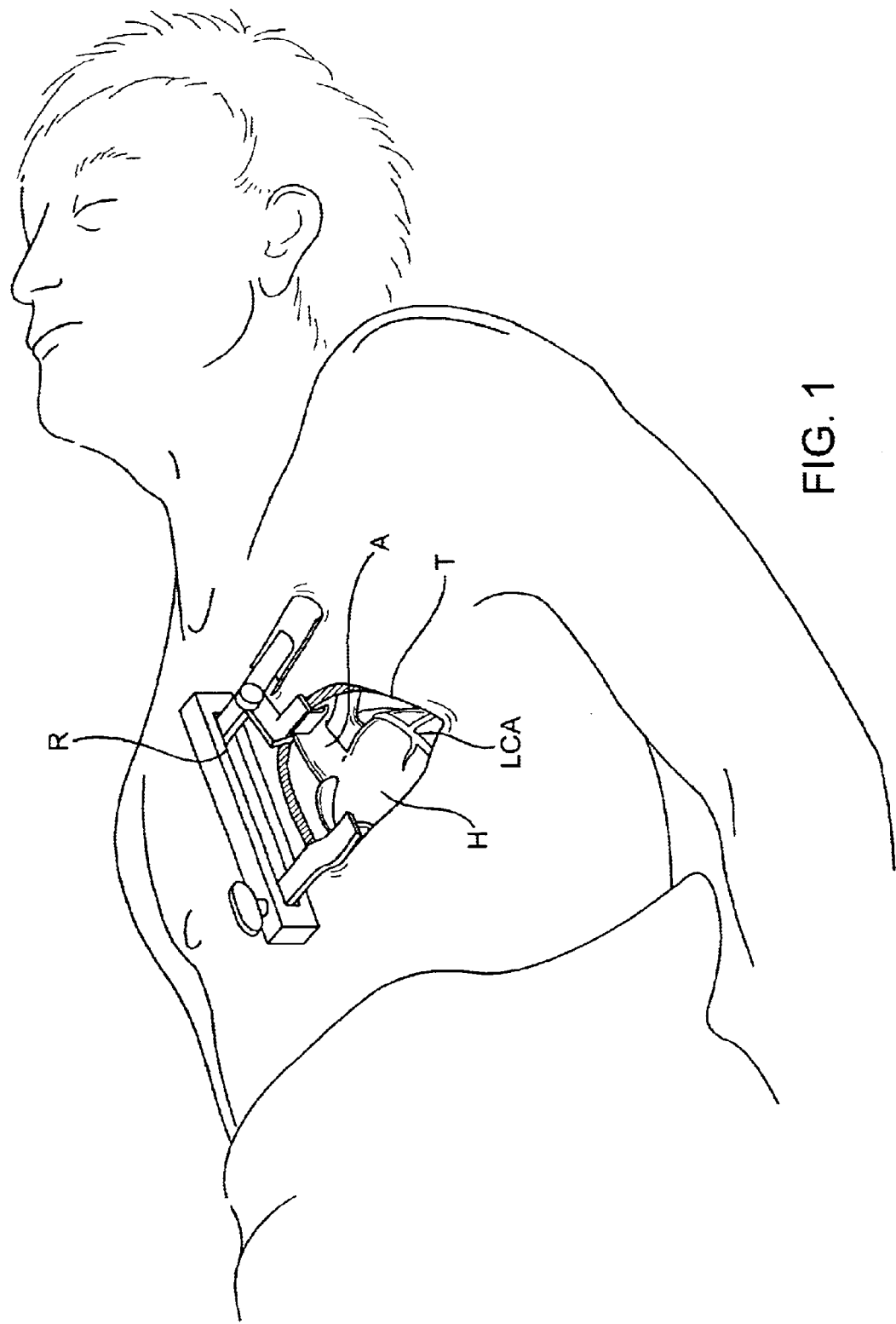
FIG. 1 is a schematic view of a patient prepared to undergo a cardiovascular surgical procedure, the patient's heart being exposed via a retractor positioned in a thoracotomy formed in the patient's chest.

FIG. 1 schematically depicts a patient who has been prepared to undergo a cardiovascular surgical procedure. A thoracotomy T formed in the patient's chest by making an incision between two ribs (not shown) provides access to the thoracic cavity. A retractor, such as the rib retractor R shown in FIG. 1, may be used to spread the ribs and increase access to the heart H and great vessels. The retractor is preferably of a type that in addition to spreading the sides of the incision along a first plane also raises one side of the incision with respect to the other side to increase the working space around the heart. Any suitable retractor may be used, for example, one of the commercially available rib retractors currently used in minimally invasive cardiac surgery. As shown in FIG. 1, the retractor R provides considerable access to the surfaces of the heart H and great vessels including the aorta A. The left side of the heart as well as the left coronary artery LCA is easily accessible via the thoracotomy T.

Referring now to FIGS. 2–5, a first embodiment of the invention provides methods and devices for placing a guide member through a coronary vessel and a heart wall so that the guide member extends into a heart chamber containing blood. In this position, the guide member provides a pathway for delivering and guiding devices into the heart chamber, for example, a system for placing a conduit to establish a blood flow path that communicates the heart chamber with the coronary vessel. Preferably, the guide member is positioned in a heart chamber that contains oxygenated blood, i.e., blood containing some level of oxygen.

Figure 2:
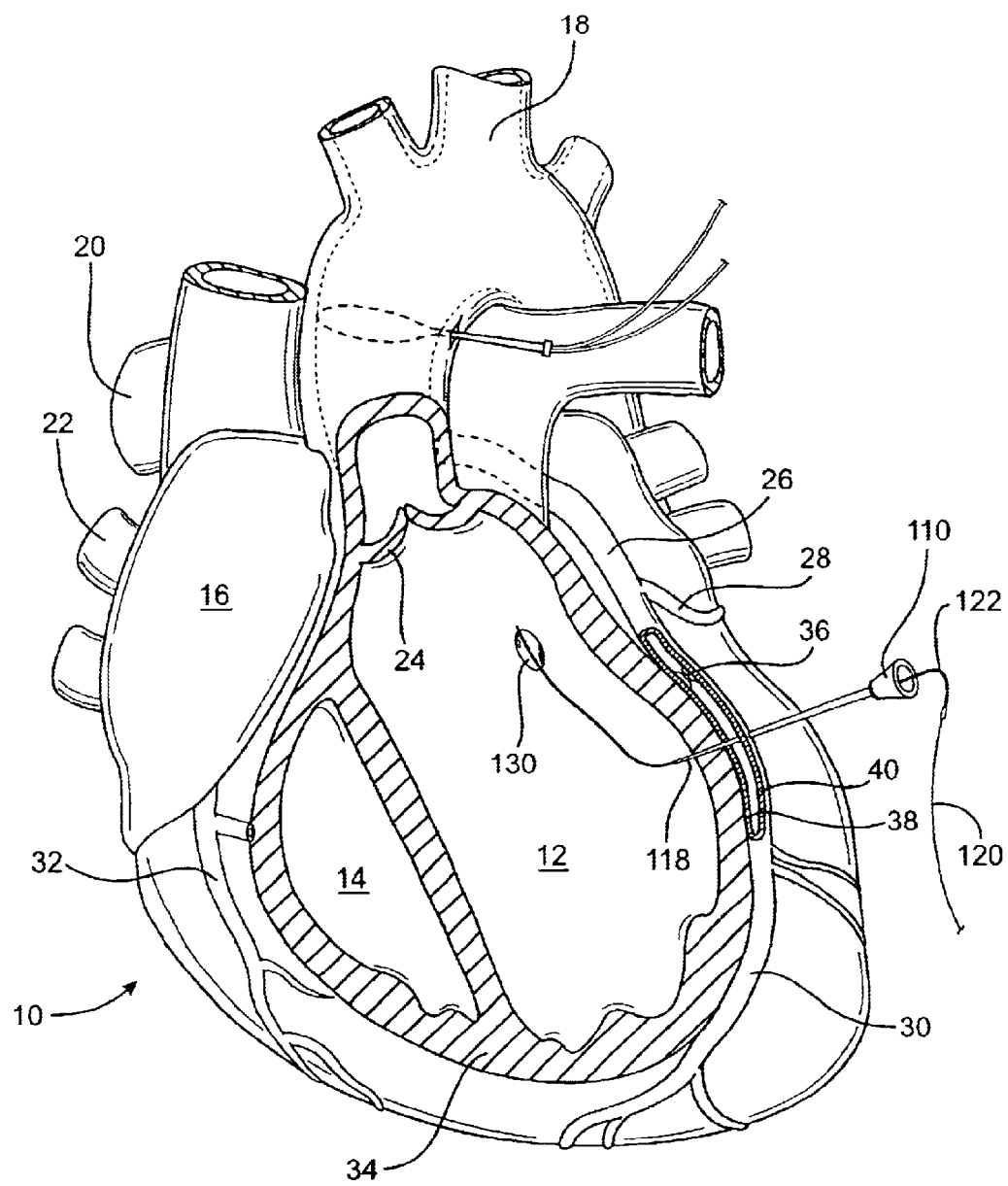
FIGS. 2–4 are perspective views sequentially illustrating the use of a system constructed according to a first embodiment of the invention for placing a guide member within a heart chamber, wherein a portion of the heart wall is broken away for clarity.

FIG. 2 is an anterior view of a heart 10 showing the left ventricle 12, right ventricle 14, right atrium 16, aorta 18, pulmonary trunk 20 and pulmonary veins 22. FIG. 2 shows the heart 10 in the diastolic (relaxed) phase of the heart cycle, during which the aortic valve 24 is closed. These views also show the left coronary artery 26 including the circumflex branch 28 and the anterior descending branch (LAD) 30. The right coronary artery 32 is visible as well. The coronary arteries 26, 28, 30, 32 run along the heart wall 34 and deliver oxygenated blood to the tissue comprising the heart wall, i.e., the epicardium, myocardium, and endocardium. A blockage or occlusion 36 is shown in the LAD 30 which results in a partial or complete blockage of the artery lumen, a condition often referred to as narrowing of the arteries. This results in inadequate or no blood flow to the heart wall tissue fed by the portion of the LAD that is downstream of the blockage 36.

The embodiment depicted in FIGS. 2–5 includes an introducer 110 positioned so as to extend through the outer and inner walls 38, 40 of the LAD 30, and through the heart wall 34 into the left ventricle 12. The introducer 110 may be a small profile, hollow shaft, for example a stainless steel hypo tube, and preferably has as small a diameter as possible in order to minimize damage to the coronary vessel. As an example, the introducer 110 may have an OD within the range of from about 0.5 mm to about 3.0 mm and an ID within the range of from about 0.4 mm to about 2.9 mm. The introducer 110 is sized to receive a guide member in a sliding manner and has an end 118 located in the heart chamber for directing the guide member through the lumen of the LAD 30 and into the ventricle 12. As explained below, the guide member is used to deliver devices into the heart chamber.

The guide member may be a single member or a plurality of members that cooperate to guide devices into the heart chamber. The embodiment illustrated in FIGS. 2–5 comprises a first guide member and a second guide member coupled together, one of the members remaining positioned in the patient's heart to introduce devices into the heart chamber. In the preferred embodiment, the first guide member is a guide wire 120 constructed of any suitable material such as stainless steel, and the second member is a catheter 122 coupled to the guide wire 120. Specifically, the proximal end 124 of the catheter 122 is coupled to the distal end 126 of the guide wire 120 by a suitable detachable connection, such as a standard leur lock. The guide wire 120 preferably has a small diameter, for example, approximately 0.25 mm, as does the catheter 122, for example, 2 French.

The distal end 128 of the catheter 122 is provided with a member that will be engaged by blood flowing from the left ventricle 12 through the aortic valve 24 into the aorta 18. In the illustrated and preferred embodiment, the member is a balloon 130 inflated via an inflation lumen (not shown) that is coupled to a source of pressurized fluid such as a syringe pump. An expandable member (e.g., balloon 130) is desirable because it may be collapsed for introduction into the heart chamber, thereby allowing a smaller opening to be formed through the wall of the coronary vessel. Of course, other types or configurations of members that will provide sufficient drag when placed in normal blood flow may be used in lieu of a balloon, e.g., an umbrella-shaped member, a soft plastic tube or a foam member. The preferred embodiment uses a member that is movable between collapsed and expanded orientations, but a non-collapsible member could be used as well.

FIG. 2 shows the catheter 122 after it has been passed through the introducer 110 to place the balloon 130 within the ventricle 12, the balloon being shown inflated to its expanded orientation. In FIG. 2 the heart 10 is in diastole; as such, the pressure in the left ventricle 12 is relatively low as it receives oxygenated blood from the left atrium (not shown). The balloon 130 remains in the left ventricle 12 until the heart goes into the systolic (contracted) phase of the heart cycle, shown in FIG. 3. The left ventricle 12 contracts to expel oxygenated blood into the aorta 18. The balloon 130 and catheter 122 are expelled from the ventricle along with the blood. The balloon 130 and catheter 122 are forced from the left ventricle 12 and pass through the aortic valve 24 into the aorta 18, which pulls a portion of the guide wire 120 into the ventricle. The position of the guide member may be monitored by ultrasound, TEE, or other means, and the guide member may be provided with a steering mechanism (not shown) if desired.

Figure 3:
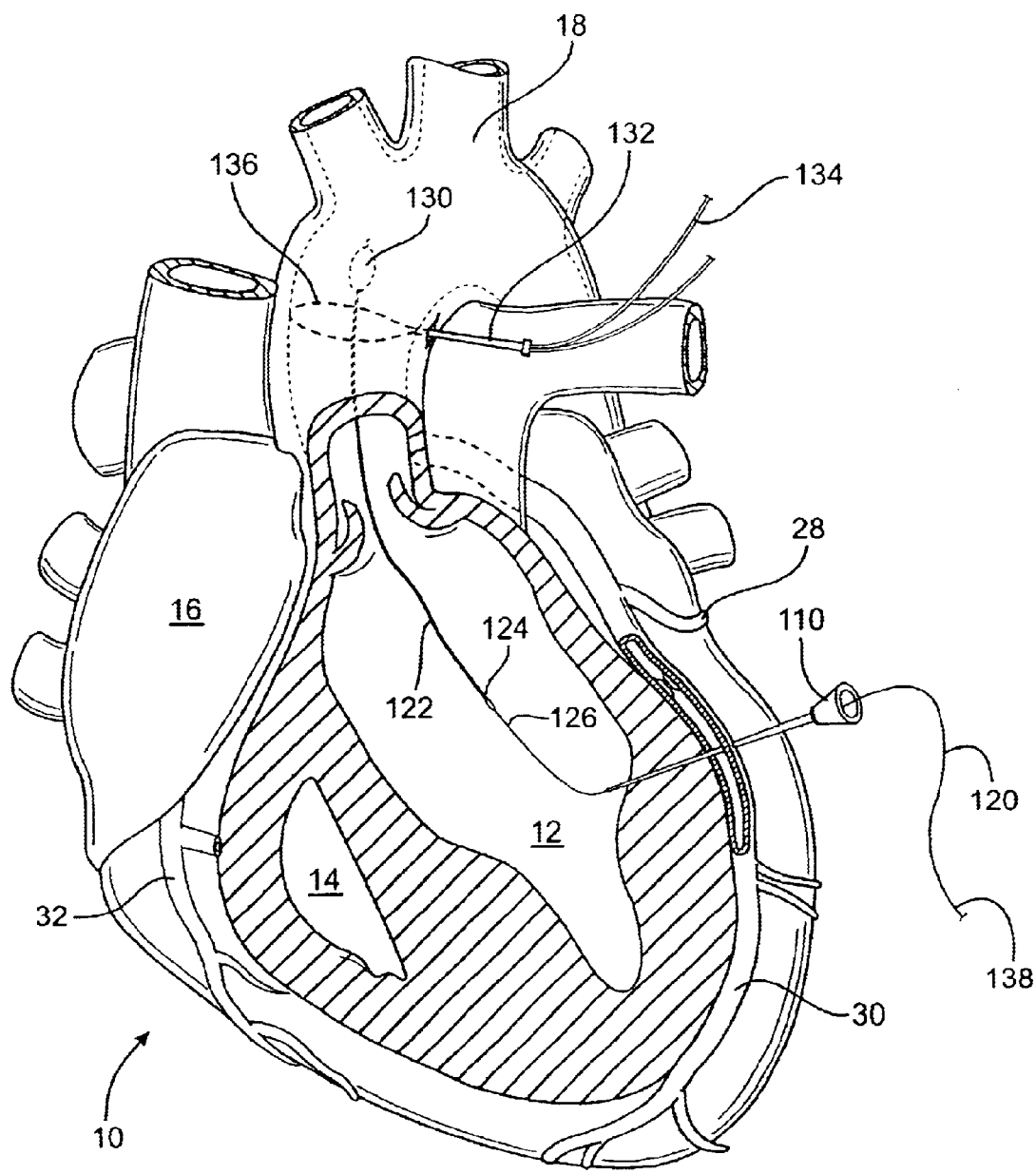

According to this embodiment, a device is provided for removing a portion of the guide member from the heart chamber. One possible device is shown in FIG. 3 and comprises a snare including an introducer sleeve 132 which is placed through an incision in the aorta 18. The sleeve 132 receives a thin wire or filament 134 configured to form a lasso 136. In the illustrated embodiment, the lasso 136 is positioned within the aorta 18 downstream of the aortic valve 24 so that the balloon 130 and catheter 122 pass through the lasso upon being forced out of the left ventricle 12 during systole. It will be understood that the device for removing a portion of the guide member from the heart may be used to retrieve the member from a different location than an opening in the aorta as shown in the Figures. For example, a magnet may be used to remove the guide member.

Figure 4:
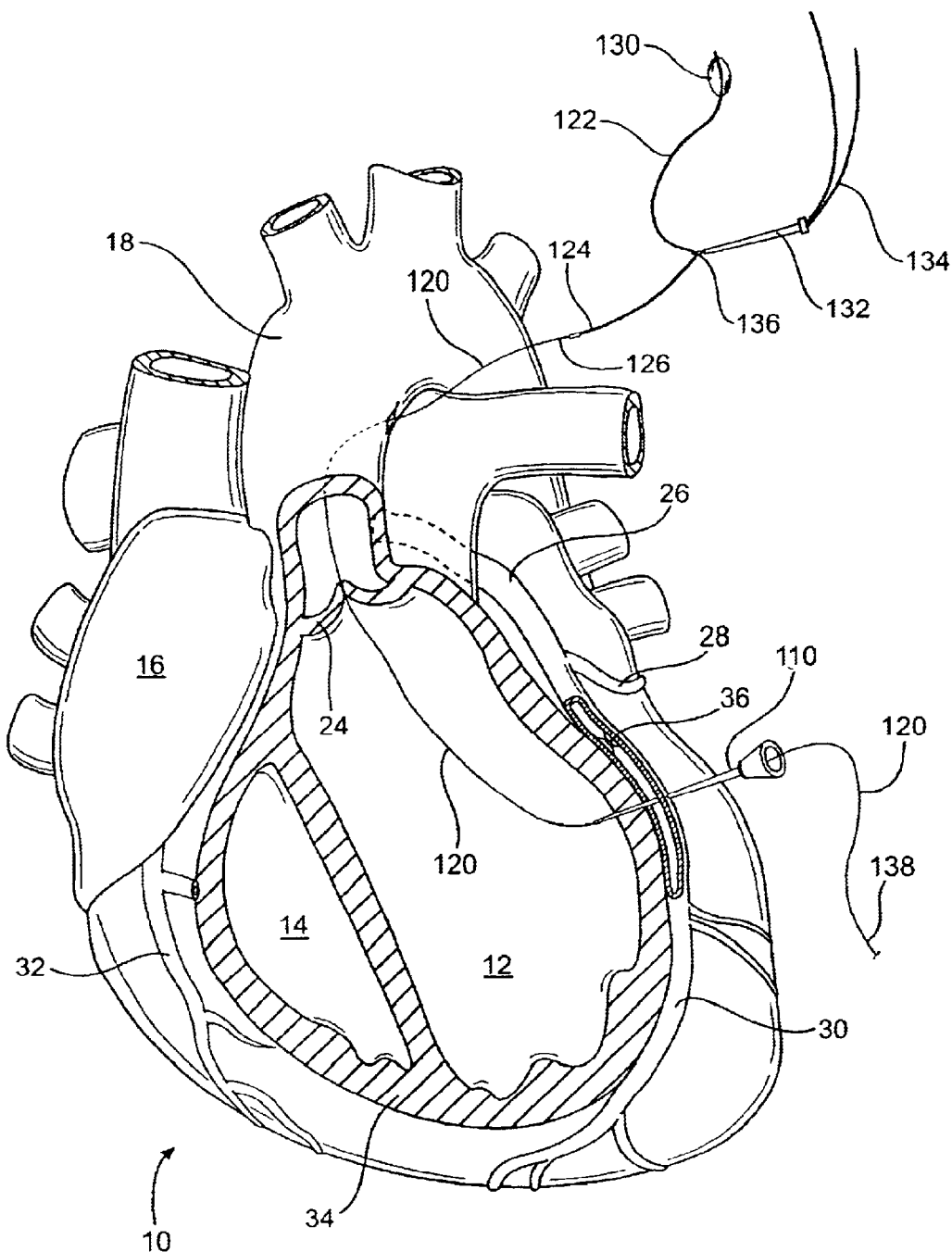
Figure 5:
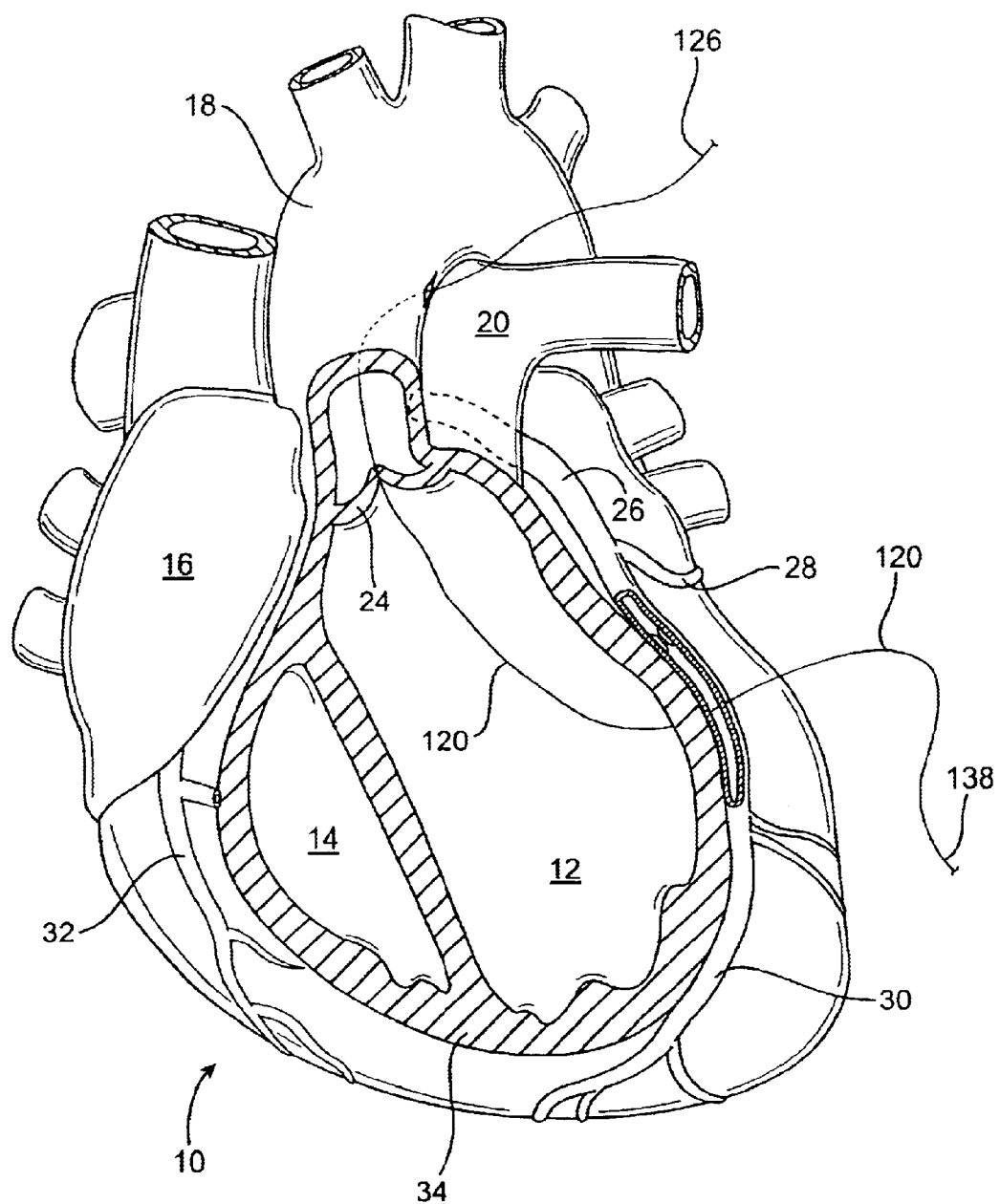
FIG. 5 is a perspective view of the heart shown in FIG. 4 after the guide member has been positioned through the heart wall so as to extend into the heart chamber and the system has been removed.

As shown in FIG. 4, which depicts the heart 10 in diastole, once the balloon 130 and catheter 122 have moved through the lasso 136, the wire 134 is withdrawn into the sleeve 132 to securely grasp the catheter 122. The entire assembly of the sleeve 132, wire 134, catheter 122 and the guide wire 120 is pulled to a location external to the heart. In the illustrated embodiment, as seen in FIG. 4, this is achieved by removing the assembly through the incision in the aorta 18, which pulls the distal end 126 of the guide wire 120 into the left ventricle 12 and then out of the aorta 18. The above step is carried out while maintaining a portion of the guide wire 120 outside the LAD 30 and the left ventricle 12. In the illustrated embodiment, a proximal section of the guide wire 120 including proximal end 138 is maintained outside the heart. As shown in FIG. 5, this embodiment of the invention results in a guide member (e.g., wire 120) extending through the wall of a coronary vessel (e.g., LAD 30) and the heart wall, into a heart chamber (e.g., left ventricle 12), and out of the heart chamber to a location external to the heart. In this position the guide member provides a pathway for delivering medical devices into the heart chamber for carrying out medical procedures.

The guide member and the introducer preferably have small enough profiles so that only a small, easily repaired incision or opening needs to be formed in the walls of the coronary vessel to place the guide member in the heart chamber, and preferably an opening that does not need to be closed by sutures. The portion of the guide member located external to the heart, e.g., distal end 126 of guide wire 120, is used to deliver medical devices into the heart chamber and the coronary vessel without going through the outer wall of the coronary vessel. As such, it is not necessary to form a large opening(s) in the wall of the coronary vessel to deliver such devices into the heart chamber. In the illustrated embodiment, devices are guided over the distal end 126 of the guide wire 120 into the aorta 18, and then into the left ventricle 12 to a desired location. In one application, the devices are then used to place a conduit (or form a channel) in the heart wall to communicate the interior of a coronary vessel with a heart chamber containing oxygenated blood.

This embodiment of the invention may of course take various forms and configurations other than those specifically depicted in FIGS. 2–5. For example, rather than using a guide member comprising a guide wire and a catheter, one of these components could be omitted. As an example, in the illustrated embodiment, the catheter could be used alone by introducing medical devices over the end of the catheter with the balloon. Also, the guide member may be sufficiently stiff to allow its introduction through the coronary vessel walls and the heart wall without an introducer, for example, by forming a conventional guide wire, catheter, cannula, etc., with a desired amount of stiffness or flexibility. The guide member may be formed of one material or comprise a composite member, such as a flexible shaft portion and a soft tip. Additionally, a device may be used to support the walls of the coronary vessel during introduction of the guide member (and/or the introducer), thereby facilitating quick and easy access and penetration of the vessel. Suitable devices for supporting the heart wall and/or vessel walls are disclosed in commonly owned, copending application, U.S. application Ser. No. 09/172,098, filed on Oct. 13, 1998 and entitled "DEVICES AND METHODS FOR USE IN PERFORMING TRANSMYOCARDIAL CORONARY BYPASS," the subject matter of which is incorporated herein by reference. The vessel may be supported internally or externally in order to facilitate placement of delivery devices through the vessel walls and the heart wall.

Figure 6:
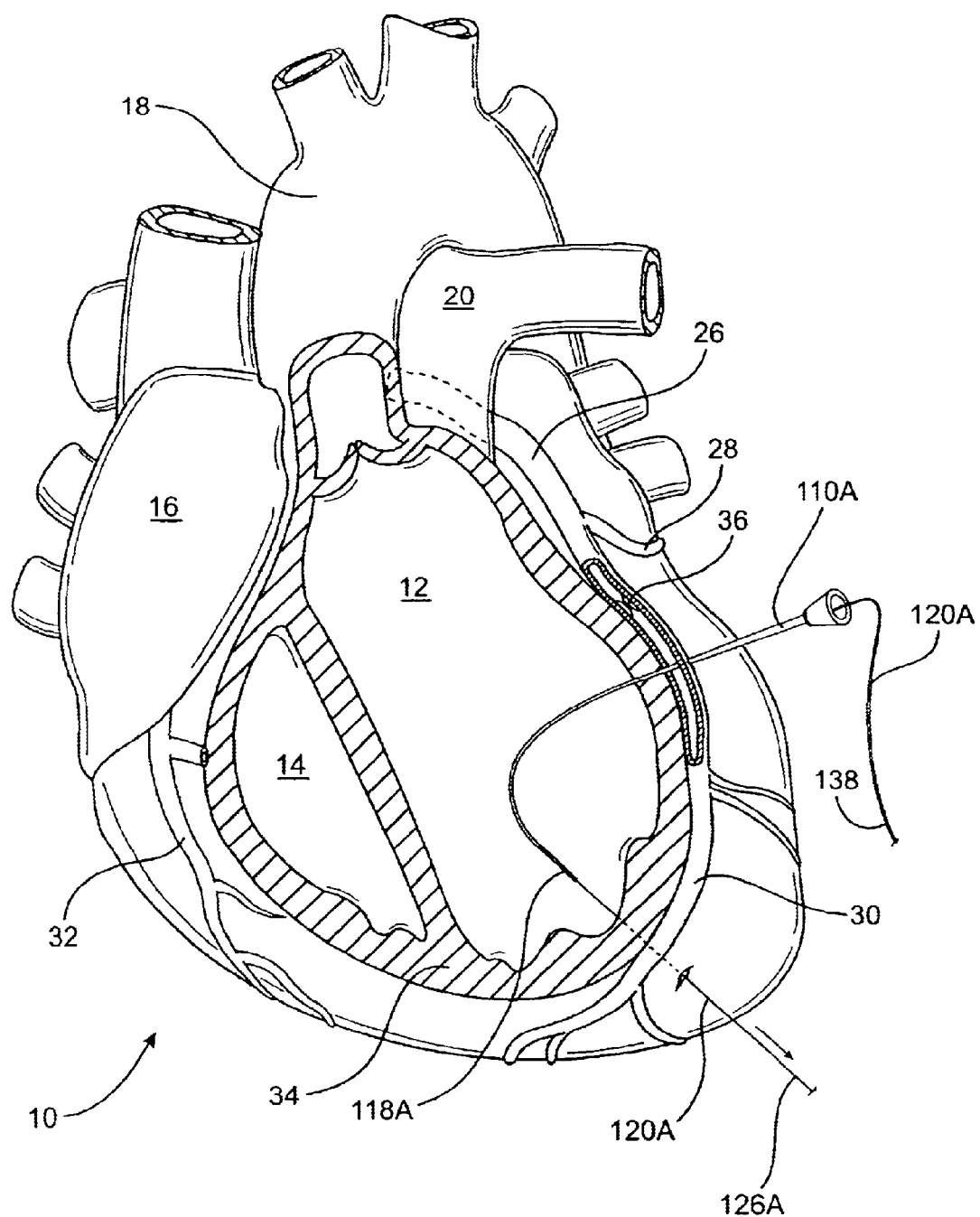
FIG. 6 is a perspective view illustrating the use of another system for placing a guide member within the heart chamber, wherein a portion of the heart wall is broken away for clarity.

An example of another system and method for placing a guide member through the wall of a heart according to this embodiment is shown in FIG. 6. As explained above with respect to FIGS. 2–5, an introducer 110A is positioned through the walls of the coronary artery LAD and a guide member is slid through the introducer. The guide member may include two guide members coupled together, as in the previous embodiment, or a single guide member. FIG. 6 shows a single guide member in the form of a guide wire 120A with a proximal end 126A and a distal end 138A.

The introducer 110A is configured to direct the guide member to a particular location within the heart. In the embodiment of FIG. 6, the introducer 110A is curved so that the distal end 118A thereof can be positioned to direct the guide member into the heart wall at a desired location, such as an area near the apex of the heart. The illustrated introducer 110A is generally J-shaped; it may, however, be shaped differently. The proximal portion of the introducer is manipulated to aim the distal end 118A in the desired direction and the guide wire 120A is passed through the introducer. The distal end 126A of the guide wire 120A exits the end 118A of the introducer 110A and passes directly through the heart wall. The guide wire 120A preferably has sufficient strength to allow the end 126A to be pushed through the tissue of the heart wall. This may be facilitated by locating the distal end 118A of the introducer 110A relatively close to the heart wall so that a relatively short length of the guide wire extends from the introducer before contacting the surface of the heart wall.

Figure 8:
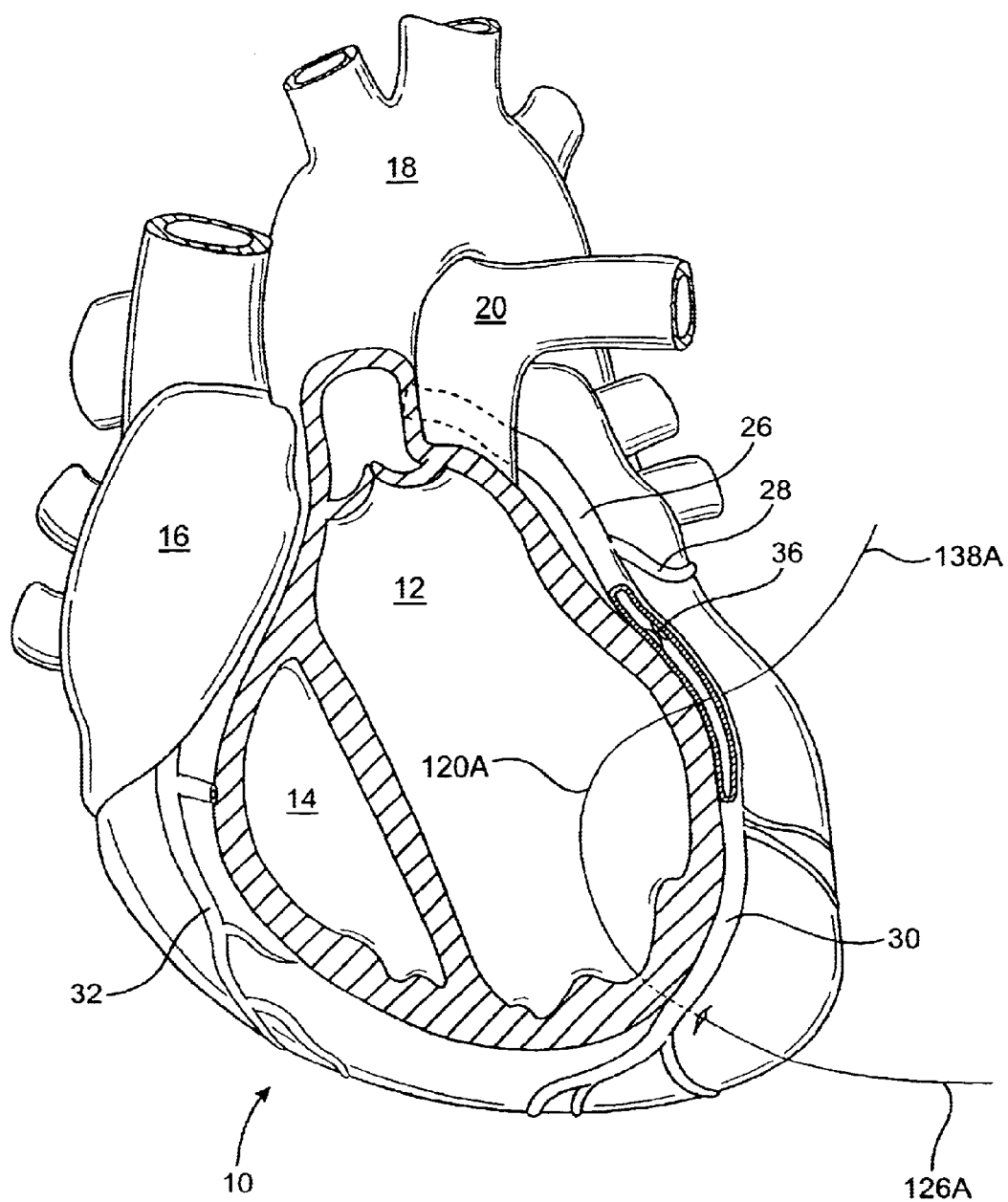
FIG. 8 is a perspective view of the heart shown in FIGS. 6 and 7 after the guide member has been positioned through the heart wall so as to extend into the heart chamber and the system has been removed.

While these steps are being carried out a portion of the guide wire 120A is maintained outside the LAD 30 and the left ventricle 12. In the illustrated embodiment, a proximal portion (including end 138A) of the guide wire 120A is maintained outside the heart. After placing the end 126A of the guide wire 120A through the coronary vessel and then into and out of the heart chamber, the introducer 110A is removed, leaving the guide wire positioned as shown in FIG. 8. One benefit of the system and method shown in FIG. 6 is that a snare (or other device) for removing a portion of the guide member from the heart chamber is not required. This obviates the need for precisely directing a portion of the guide member to a specific location within (or without) the heart chamber to allow its removal.

Additionally, while either the introducer or the guide member may be preshaped to direct the guide member to a particular area within the heart chamber, it should be noted that the introducer may be in the form of curved hollow needle that is sized and configured to be passed through the coronary vessel and the heart wall into the heart chamber, and then out of the heart chamber. The introducer thus may extend from outside the heart chamber, into the heart chamber, and then out of the heart chamber. A guide member or conduit delivery device may then be positioned in the heart chamber using the introducer.

Figure 7:
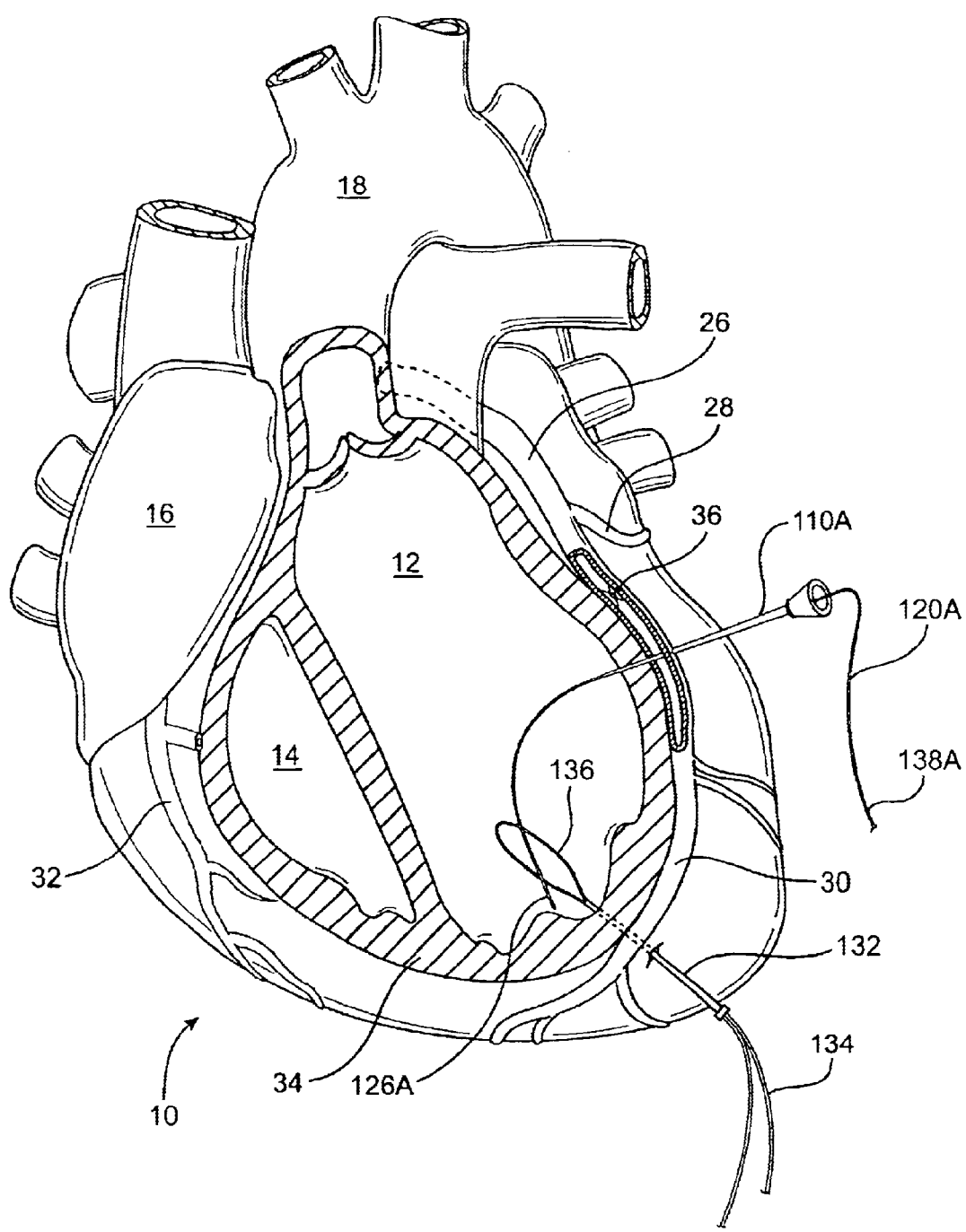
FIG. 7 is a perspective view illustrating the use of yet another system for placing a guide member within the heart chamber, wherein a portion of the heart wall is broken away for clarity.

In an alternative system and method, shown in FIG. 7, the guide member is removed from the heart chamber by a snare or like device. An introducer 110 is used in the manner described above with respect to FIGS. 2–5 to place the distal end 126A of the guide wire 120A within the left ventricle 12 at a desired location, for example, adjacent the apex of the heart. The guide wire 120A is preferably preshaped to assume a desired position when inserted into the heart chamber. From here the distal end 126A of the guide wire 120A is removed to a location external to the heart by a snare assembly comprising components 132, 134, 136 that are used to grasp and remove a portion of the guide wire 120A from the left ventricle 12. In this and the previous embodiments, the guide member may be manipulated or steered to a desired location by a suitable mechanism (not shown), or formed of a shape memory alloy that directs the guide member to the desired location after insertion into the heart.

As in the previous embodiments, a portion of the guide wire 120A is removed while maintaining another portion of the guide wire outside the LAD 30 and the left ventricle 12. Specifically, as in the previous embodiment, a proximal section of the guide wire 120A including end 138A is preferably maintained outside the heart. Use of the system shown in FIG. 7 thus results in a guide member extending through the wall of the LAD 30 and the heart wall into the left ventricle 12, and out of the ventricle to a location external to the heart, for example, as shown in FIG. 8.

A guide member placed according to the systems and methods described above provides a pathway for delivering medical devices into the heart chamber without passing the devices through the walls of the coronary artery. However, it will be recognized that the systems and methods illustrated in FIGS. 2–8 are only exemplary and that this embodiment of the invention encompasses placing a guide member within a patient's heart so that different medical devices may be delivered into a heart chamber. The particular procedure carried out or the systems or devices used to place the guide member will vary depending on the application.

Figures 9, 9A:
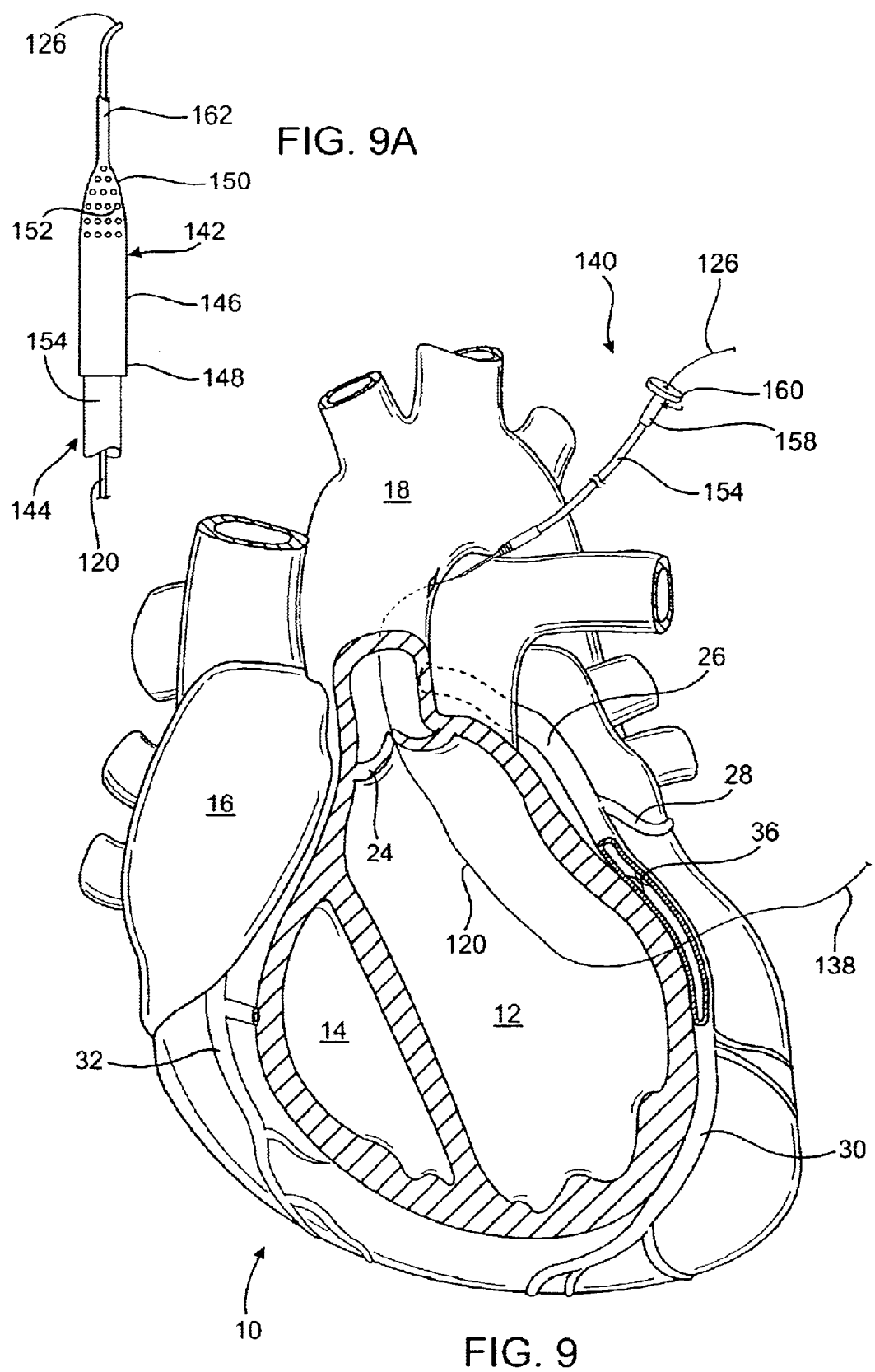
FIG. 9 is a perspective view illustrating a conduit placement system constructed according to a second embodiment of the invention for placing a conduit in a heart wall, the system being used with a guide member positioned in the heart chamber as shown in FIG. 5.
FIG. 9A is an enlarged view of a portion of the system shown in FIG. 9.

In one preferred application, a guide member positioned as discussed above is used to deliver a conduit (or form a channel) that forms a blood flow path between a heart chamber and the interior of a coronary vessel. FIGS. 9–13A illustrate a delivery system and method constructed according to a second embodiment of the invention for placing a conduit within the heart wall to communicate the left ventricle 12 with the LAD 30. A delivery system is designated by the reference numeral 140 and comprises a conduit 142 supported on a delivery device 144. The conduit 142 is preferably a rigid (i.e., not expandable) tubular element including a body portion 146 having a first end 148 and a second end 150. The conduit body portion 146 includes one or more openings 152 passing through the wall thereof. In the preferred embodiment, the body portion 146 has a plurality of holes located adjacent the second end 150, which end is preferably tapered as shown in FIGS. 9 and 9A. Blood flows into the interior of the conduit 142 via the first end 148 and out of the conduit through openings 152 into the interior of the LAD 30.

In the preferred construction, the delivery device comprises a shaft 154 (FIG. 9A) having a substantially complementarily shaped exterior to support the conduit 142 during introduction into the left ventricle 12 and delivery into the heart wall 34. The shaft 154 has an elongated body that extends beyond the length of the conduit 142. The elongated body is slidable over a guide member (guide wire 120 in the Figures) that has been positioned in a manner corresponding to that described above with respect to FIG. 5. The body of the shaft 154 has a clamp 158 which secures the shaft to the guide wire 120 in order to deliver the conduit 142 into the heart wall 34. The clamp 158 has a rotatable knob 160 to selectively clamp the shaft 154 to the guide wire 120. Any other suitable mechanism may be used to couple the shaft 154 to the guide wire 120. FIG. 9 shows the shaft 154 secured to the guide wire 120 and ready to be introduced into the left ventricle 12 via the opening in the aorta 18.

Figures 10, 10A:
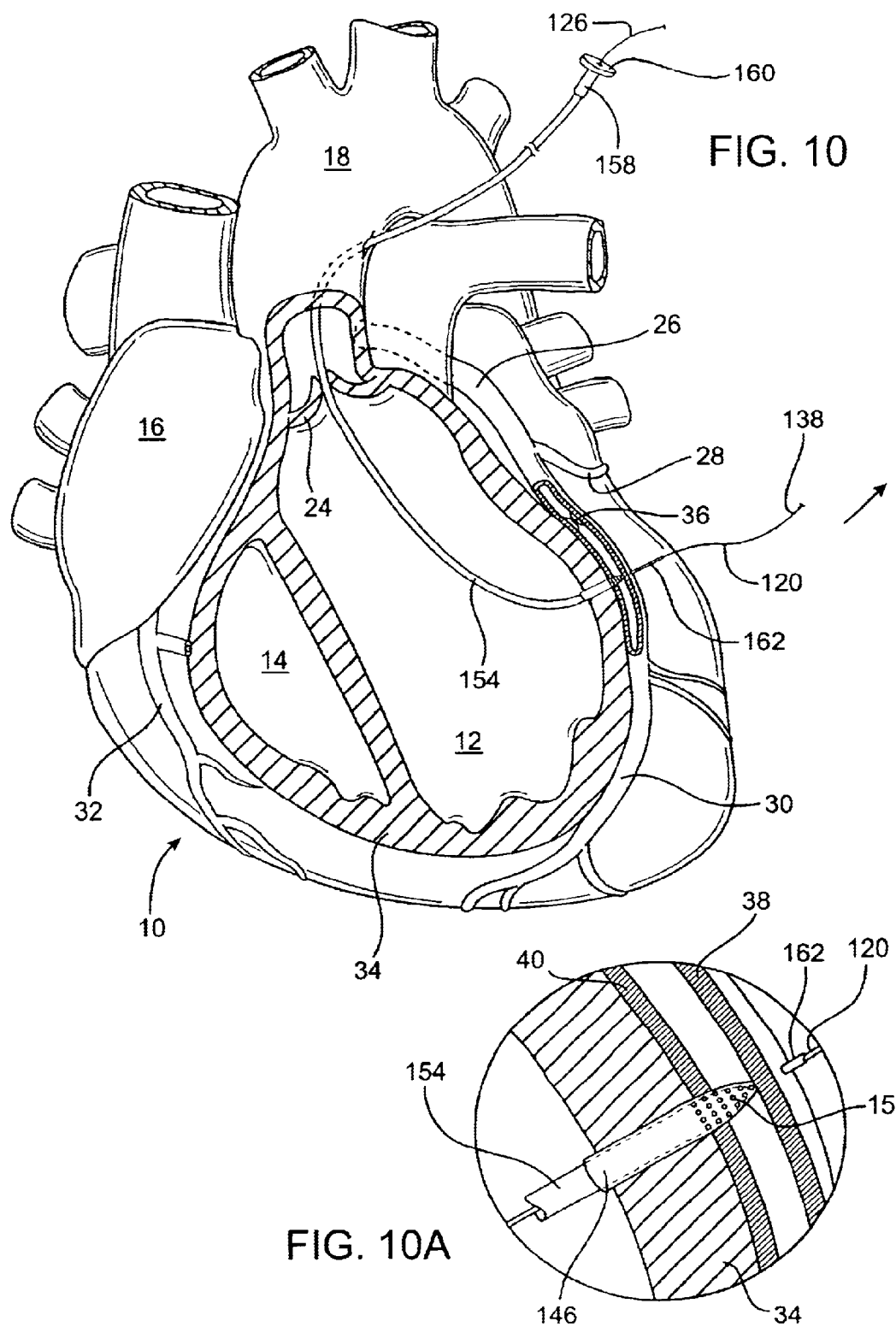
FIGS. 10 and 11 are perspective views sequentially illustrating using the system shown in FIG. 9 to place a conduit in the heart wall.
FIGS. 10A and 11A are enlarged sectional views of the system shown in FIGS. 10 and 11, respectively.

Once the shaft 154 and conduit 142 have been slid over the distal end 126 of the guide wire 120 and secured thereto by the clamp 158, the proximal end 138 of the guide wire 120 is pulled in the direction of the arrow in FIG. 10. This moves the guide wire 120, shaft 154 and conduit 142 into the aorta 18, past the aortic valve 24 and into the left ventricle 12. As the proximal end 138 of the guide wire 120 is pulled further, the conduit 142 enters the heart wall 34, as shown in FIGS. 10–10A. The position of the conduit 142 relative to the heart wall 34 and the LAD 30 can be controlled by manipulating the distal end 126 of the guide wire 120 or the proximal end of the shaft 154 (or end 138 of the wire). The position of the conduit 142 within the heart wall 34 thus can be selectively adjusted by pulling or pushing an end of the guide wire 120 (or shaft 154) with respect to the heart wall.

Figures 11, 11A:
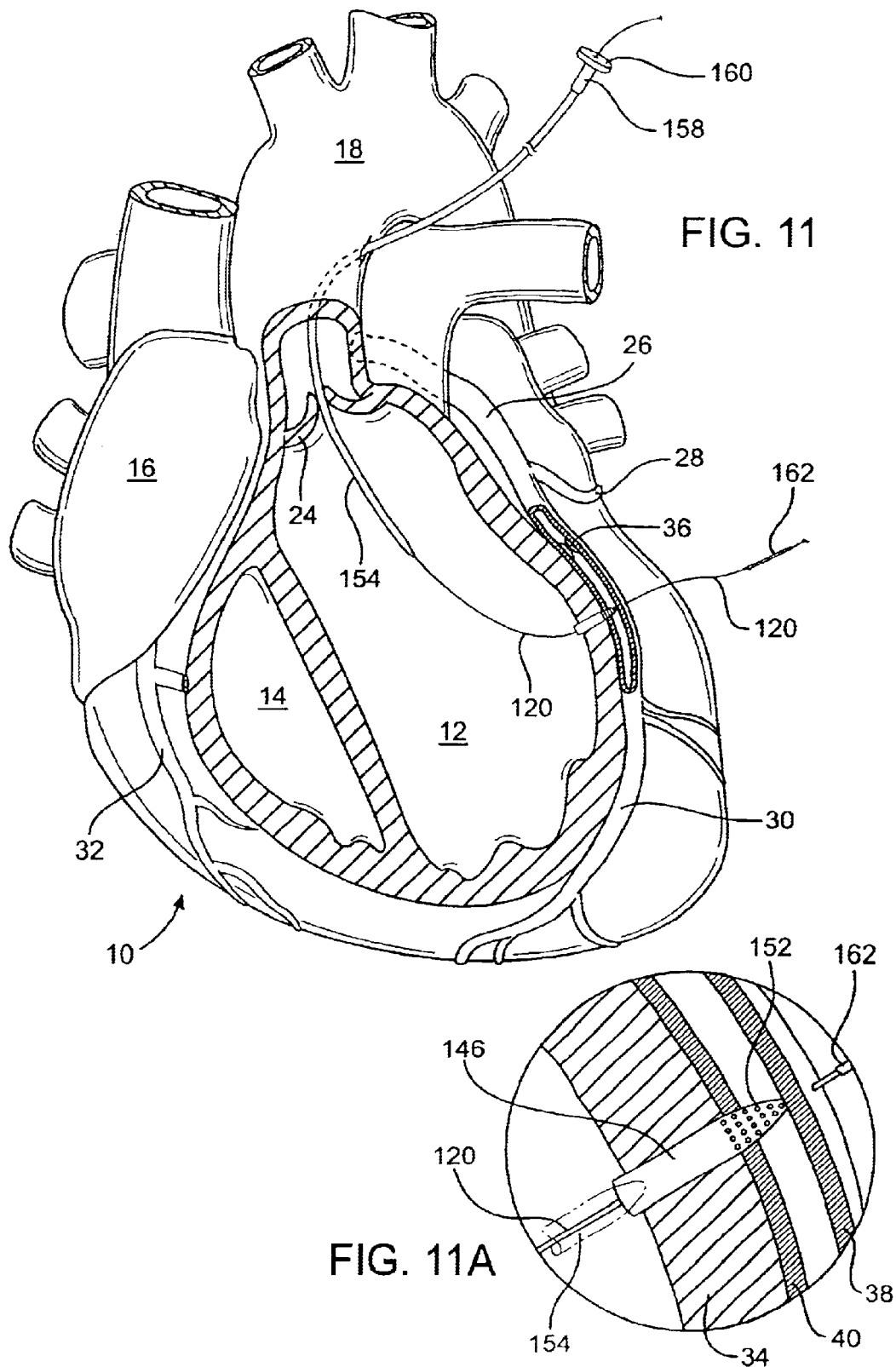

FIG. 10A shows the conduit 142 positioned in the heart wall 34 so that a portion of the second end 150 is located within the lumen of the LAD 30. In this embodiment at least some of the openings 152 are located within the LAD 30 and deliver blood from the left ventricle 12 into the artery. Once the conduit has been placed in its desired position, for example, the position shown in FIG. 10A, the shaft 154 is removed from the conduit by pulling the shaft into the left ventricle 12 and toward the aorta 18. This may be accomplished in various ways. For example, as shown in FIG. 11, the clamp 158 may be disengaged from the guide wire 120 by rotating the knob 160 to allow the shaft 154 to be slid off the proximal end of the wire in the direction of the arrow. Alternatively, the shaft 154 and the guide wire 120 may be removed as a unit by pulling the elements through the conduit 142, into the left ventricle 12 and out of the aorta 18, thereby obviating the need to release the clamp 158 from the wire 120.

In the illustrated embodiment, the second end 150 of the conduit 142 includes a low profile end 162 with a small diameter that is easily passed through the outer wall 38 of the LAD 30 after the conduit has been moved to the position of FIGS. 10–10A. The end 162 preferably comprises a thin-walled section of tubing that collapses or folds and conforms to the exterior of the guide wire 120. The end 162 may be separate from or integral with the material forming the conduit 142. In the preferred construction shown in the Figures, the-end 162 is detachable from the conduit 142 by suitable means, e.g., a perforated or scored section. As such, when the conduit 142 is positioned within the heart wall, the portion of the end that is outside the LAD 30 may be grasped and removed by pulling it in the direction of the arrow in FIG. 11, preferably while holding the proximal end 138 of the guide wire 120 or the portion of the shaft 154 located external to the heart, as shown in FIG. 11. Alternatively, the end 162 may be omitted with the conduit 142 open or closed at the end positioned in the artery.

Figure 12:
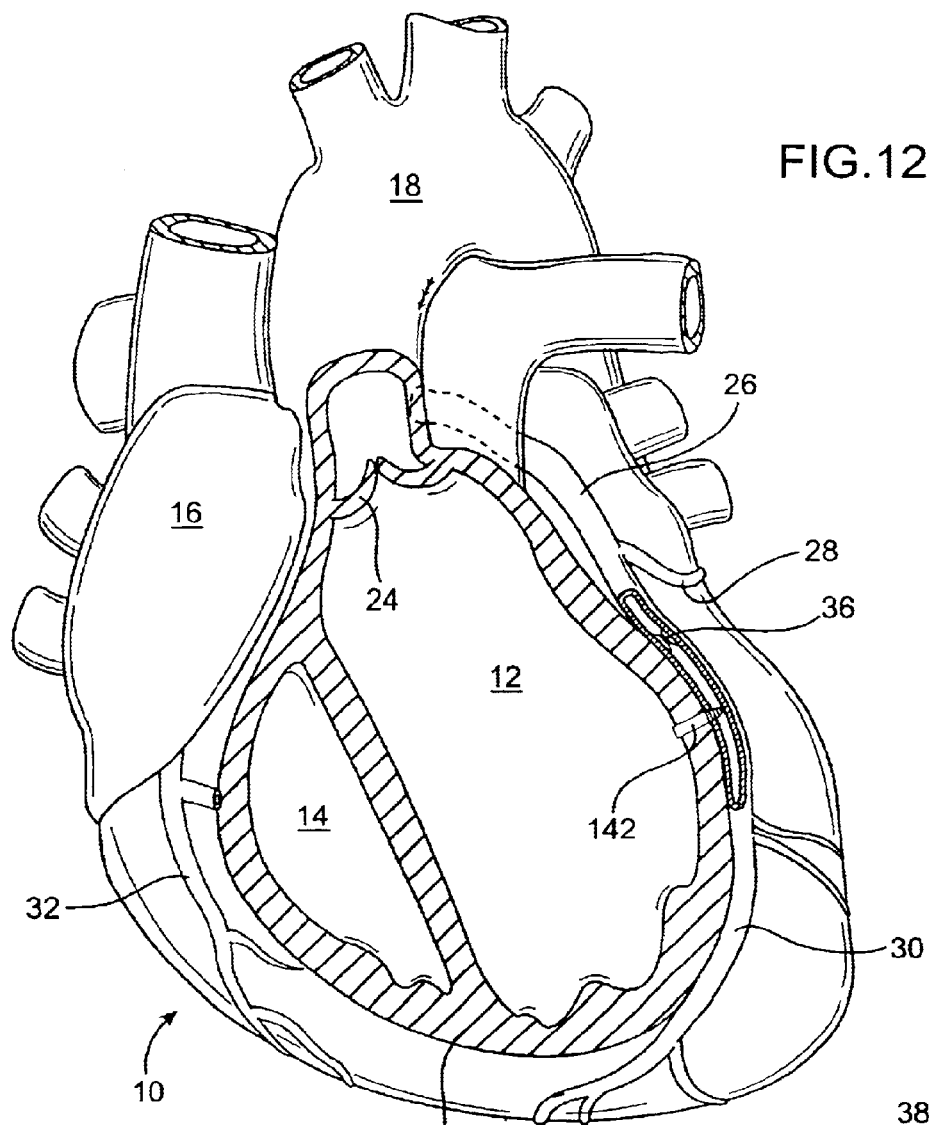
FIG. 12 is a perspective view illustrating the conduit placed in the heart wall by the system shown in FIGS. 9–11.
Figure 12A:
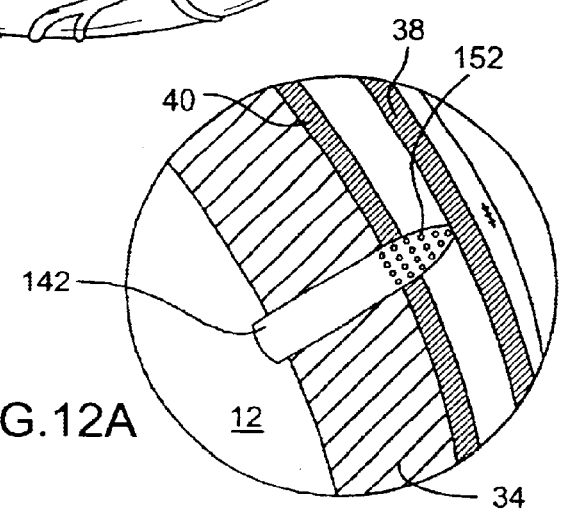
FIG. 12A is an enlarged sectional view of the conduit of FIG. 12.

After removing the end 162 from the conduit 142, the opening in the outer wall 38 of LAD 30 is repaired as shown in FIGS. 12–12A. If the shaft 154 has been removed previously without removing the guide wire 120, the guide wire is removed by pulling it out of the opening in the aorta 18 or the openings in the walls of the LAD 30. The opening in the aorta is then repaired. The resulting placement of the conduit 142 provides a blood flow path between the left ventricle 12 and the LAD 30, which path is located distal to the occlusion 36 so that the myocardial tissue fed by the distal portion of the LAD is perfused.

The illustrated conduit 142 is preferably formed of a rigid material that is strong enough to resist the force exerted by the myocardial tissue during systole so that the blood flow path is not blocked when the heart contracts. The conduit 142 may be formed of various materials, for example, stainless steel, titanium, nitinol, polymers, ceramics, etc. Alternatively, the conduit may be constructed of a material that partially collapses when the heart contracts during systole and returns to its normal configuration during diastole, or the conduit may achieve specific flow characteristics by regulating blood flow with a valve or other means.

Additionally, the conduit may have a constant cross-section fully open at both ends, and it may be provided with any size, shape and number of openings 152 depending on the desired flow characteristics. For example, the openings 152 may be located along the entire length or only a portion of the length of the conduit 142. Moreover, the shape of the conduit itself may be varied from that shown in the Figures. For example, the conduit 142 may have a constant cross-section over its length rather than a tapered portion, or one or both ends of the conduit may have enlarged portions, e.g., flanges, extensions or outwardly tapered sides for aiding in engaging the conduit with the wall of the heart or the wall of the coronary vessel. As a further example, the conduit may have an enlarged central portion with reduced size ends, and the central portion may act as a blood reservoir. Further, while the conduit 142 is shown extended into the lumen of the LAD 30, it may instead be flush with or slightly below the inner wall 40 of the LAD 30 (or flush with the surface of occlusion 36 in the LAD 30).

Similarly, although in the preferred system and method the shaft 154 and the conduit 142 are coupled to the guide wire 120 so as to move therewith, the system may be used without coupling these elements. For example, the guide wire 120 may be positioned as shown and held while the delivery system 140 is slid over the wire into the aorta and then into the left ventricle 12. The conduit 142 may then be pushed into the heart wall 12. However, it is preferred to secure the guide wire 120 to the shaft 154 so that these components can be pulled into the heart chamber as a unitary assembly. This avoids having to push the shaft and conduit over the wire, which exerts force against the guide wire and tends to pull the wire toward the chamber or against the walls of the artery. Nonetheless, the system and method may be used by sliding or otherwise moving the delivery device relative to the guide wire.

FIGS. 13–17A show another preferred system and method for delivering a conduit into a heart chamber and placing the conduit in the heart wall to communicate the heart chamber with the interior of a coronary vessel. As shown in FIG. 13A, the system is designated by the reference numeral 170 and comprises a conduit 172 supported on a delivery device 174. The conduit 172 is preferably an expandable tubular member in the form of a stent including a plurality of elements 176 that move relative to each other as the stent moves between collapsed and expanded orientations. The conduit 172 preferably comprises a stent having a plurality of struts that move to a load supporting position when the stent assumes its expanded orientation, the struts defining a plurality of open areas through which blood may flow. In the illustrated embodiment, the conduit 172 is delivered into the left ventricle and placed in the heart wall while in its collapsed orientation, and then is opened to its expanded orientation.

The conduit 172 is supported on the delivery device 174 in its collapsed orientation. In the illustrated embodiment, the conduit 172 is a balloon-expandable stent; thus, the device 174 comprises a balloon 178 that is inflated via an inflation lumen that communicates with a source of pressurized fluid (not shown). Alternatively, the stent could be expanded by a non-inflatable mechanism rather than a balloon. As a further alternative, the conduit 172 may be in the form of a self-expanding stent that is retained in its collapsed orientation by a cover or sleeve disposed around the stent. In either case, it is desirable to cover the conduit 172 during delivery into the left ventricle and the heart wall to prevent the elements 176 from snagging or damaging tissue as they are passed into heart. As such, if the conduit comprises a balloon-expandable stent as illustrated, a sheath 180 is preferably placed over the conduit to cover the elements 176.

The delivery device 174 comprises an elongated shaft provided with a mechanism for securing the device to the guide wire 120A. A preferred mechanism is supported by a Y-connector 182 and includes a clamp 184 in the form of a rotatable knob that is operated as described above with respect to the embodiment of FIGS. 914 12A. The clamp 184 is used to secure the shaft to the guide wire 120A so that the components can be manipulated as a unitary assembly. The Y-connector 182 may be provided with a leg 186 for being coupled to a source of pressurized fluid, such as a syringe pump. The elongated shaft of the delivery device 174 is slidable over the guide wire 120A which, in the illustrated embodiment, has been positioned in a manner corresponding to that described above with respect to FIG. 8. The clamp 184 secures the shaft 174 to the guide wire 120A in order to deliver the conduit 172 into the heart wall 34. The clamp 184 has a rotatable knob to selectively clamp the shaft 174 to the guide wire 120A. Any other suitable mechanism may be used to attach the shaft 174 to the guide wire 120A. FIG. 13 shows the shaft 154 secured to the guide wire 120 and in the process of being introduced into the left ventricle 12 via the opening in the aorta 18.

Figures 14, 14A:
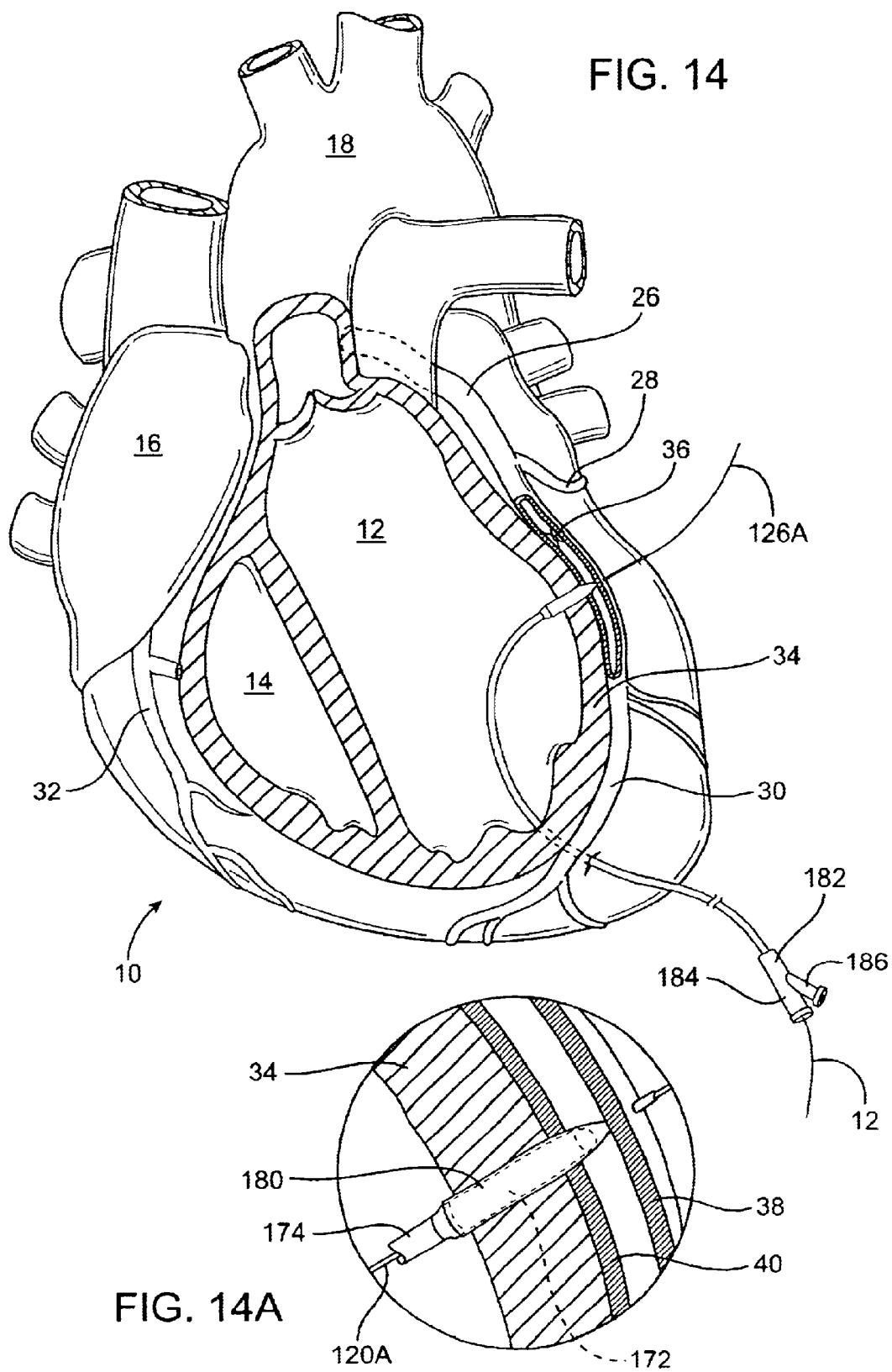

Once the shaft 174 and conduit 172 have been slid over the proximal end 138A of the guide wire 120A and secured thereto by the clamp 184, the distal end 126A of the guide wire is pulled in the direction of the arrow in FIG. 13. This moves the guide wire 120A, shaft 174 and conduit 172 into the left ventricle 12. As the distal end 126A of the guide wire 120A is pulled further, the conduit 172 enters the heart wall 34 with the end of the sheath 180 dilating the opening, as shown in FIGS. 14–14A. The position of the conduit 172 relative to the heart wall 34 and the LAD 30 can be controlled by manipulating the proximal end of the shaft and the distal end 126A of the guide wire 120A. That is, the position of the conduit 172 within the heart wall 34 can be selectively adjusted by pulling one end of the guide wire 120A (or and end of the shaft 154) toward or away from the heart wall.

FIG. 14A shows the conduit 172 positioned in the heart wall 34 so that an end 188 of the conduit is located within the lumen of the LAD 30. At least some of the openings defined between the stent elements 176 are located within the LAD 30 so that blood may flow into the LAD through the end and the wall of the conduit. Once the conduit has been placed in its desired position, for example, the position shown in FIG. 14A, the sheath 180 is removed to expose the conduit to the heart wall tissue. The sheath may be removed in any suitable manner. In the illustrated embodiment, the sheath 180 has an end 190 which can be grasped outside the LAD 30 and pulled. The entire sheath is preferably formed of a soft, collapsible material to permit the sheath to be folded or bunched up in order to pass through the opening in the walls of the LAD 30. Suitable materials include urethane, polyethylene, polytetrafluoroethylene, etc.

Figures 16, 16A:
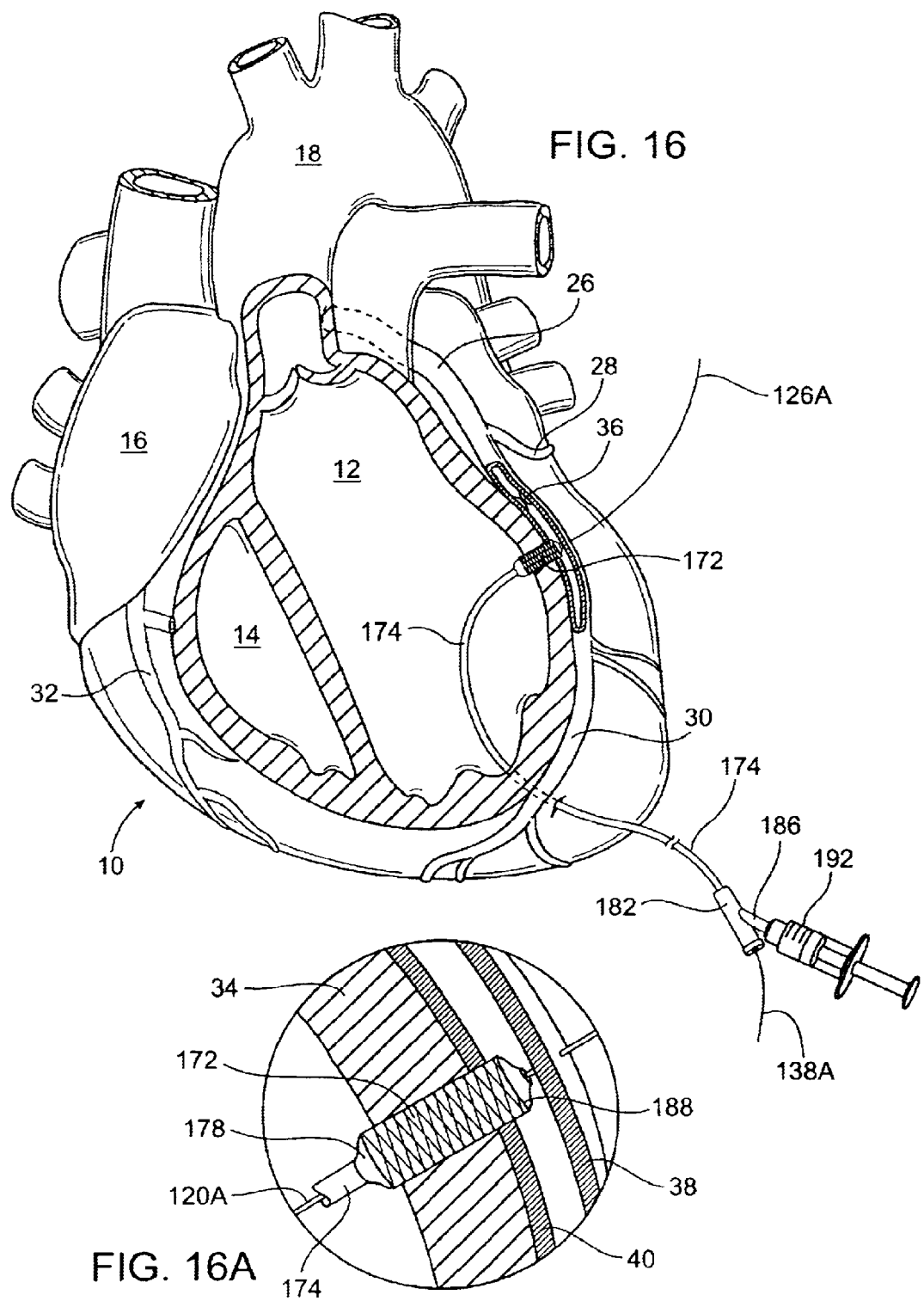

FIG. 15 shows the sheath 180 after it has been removed from the conduit 172 and the LAD 30. Removing the sheath 180 exposes the conduit 172 and results in tissue moving into the spaces between the stent elements 176, which helps retains the conduit in position. FIG. 15A shows the conduit 172 once the sheath 180 has been removed. Next, in the case of an expandable conduit such as that shown in FIGS. 15–15A, a mechanism is utilized to expand the stent elements 176, preferably to their maximum strength position. One suitable mechanism is shown in FIG. 16A and includes the balloon 178. The balloon 178 is inflated by a source of pressurized fluid, such as syringe 192, coupled to inflation lumen 186. The syringe 192 is actuated to inflate the balloon 178 and expand the conduit 172 to the orientation shown in FIGS. 16–16A.

Next, the syringe 192 is actuated to take down the balloon 178 for removal from the interior of the conduit 172. The deflated balloon can be pulled into the ventricle 12 and removed through the opening in the heart wall (adjacent the apex in the Figures). This may be accomplished by disengaging the clamp 184 from the guide wire 120A to allow the shaft 174 and balloon 178 to be slid off of the wire (not shown). The guide wire 120A may then be removed by pulling either end through the chamber. Alternatively, the shaft 174, balloon 178 and guide wire 120A may be removed as a unit by pulling the elements (after the balloon has been deflated) through the conduit 172 and then into and out of the left ventricle 12.

Figure 17:
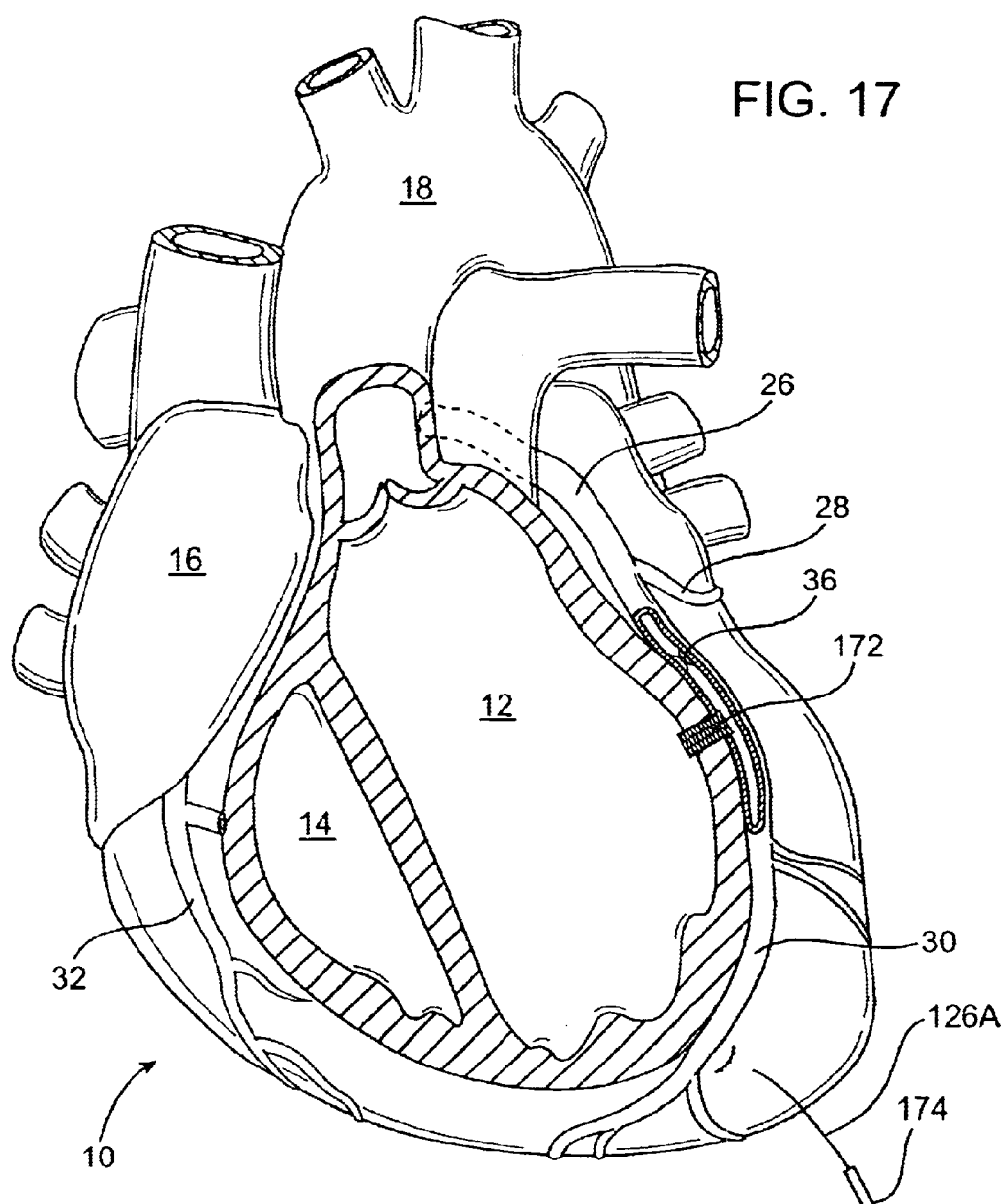
FIG. 17 is a perspective view illustrating the conduit placed in the heart wall by the system shown in FIGS. 13–16.
Figure 17A:
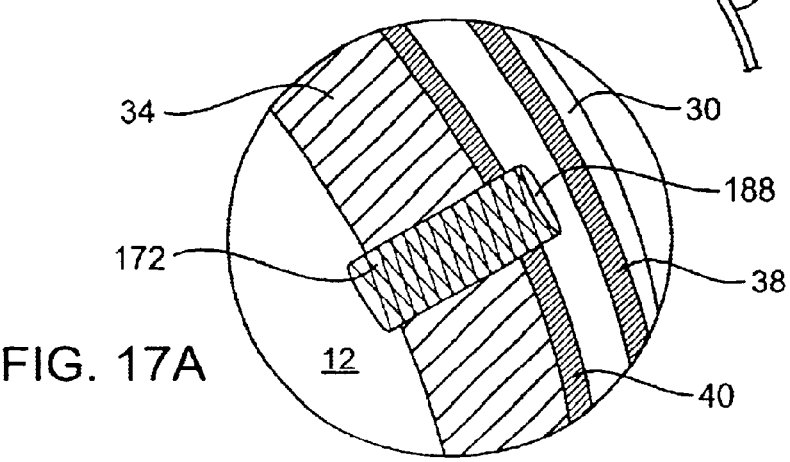
FIG. 17A is an enlarged sectional view of the conduit of FIG. 17.

FIGS. 17–17A show the conduit 172 expanded and positioned in the heart wall after the delivery system has been removed from the heart. After the conduit 172 has been fully expanded it firmly engages the tissue of the heart wall. The conduit 172, because it is constructed as a stent, remains expanded despite the force exerted against it by the heart wall during the systolic phase of the heart cycle. In the illustrated embodiment, the size of the conduit is constant over its cross-section and the ends of the conduit extend slightly into the lumen of the LAD 30 and the left ventricle 12. It should be recognized though that the conduit may have a size or shape that varies over its length, and may be positioned with one or both ends extending within, beyond or flush with the ventricle and coronary surfaces of the heart wall.

Moreover, it will be appreciated that FIGS. 9–12A and FIGS. 13–17A respectively illustrate two independent conduit delivery systems and methods for placing a conduit within the heart wall to communicate the left ventricle with a coronary artery. The conduit delivery system and method of FIGS. 9–12A are disclosed in connection with a guide member placed as shown in FIG. 5, while the system and method of FIGS. 13–17A are disclosed in connection with a guide member placed as shown in FIG. 8. It will be appreciated, however, that such description is for explanatory purposes as each conduit delivery system and method may be used with a guide member placed by any manner other than those disclosed herein. Similarly, the specific construction and configuration of the conduit and delivery system may be different from those specifically illustrated.

FIGS. 18A–21 show systems and methods for placing a conduit in the heart wall so as to communicate a heart chamber with a coronary vessel according to a third embodiment of the invention. In this embodiment, the conduit has a generally funnel-shaped configuration in that one end of the conduit is larger than the other end of the conduit. The conduit is positioned in the heart wall to communicate a heart chamber with a coronary vessel. The larger end of the conduit is preferably positioned in the heart chamber and the smaller end is positioned in the vessel, although one or both ends could be flush with or within the heart wall.

Referring to FIGS. 18A–18F, a conduit delivery system indicated by reference numeral 200 includes a conduit 202 supported on a delivery device 204. The conduit 202 is similar to the conduit 172 in that it is in the form of a stent including a plurality of elements 206 that move relative to each other as the stent moves to its expanded orientation. The conduit 202 preferably assumes a maximum load supporting position when fully expanded. Blood may flow through a plurality of open areas defined between the stent elements 206.

The conduit 202 is supported on the delivery device 204 which itself is supported on a guide member, such as guide wire 208. The conduit 202 is supported in a collapsed orientation and, in the illustrated embodiment, is expanded by a balloon 210 that is inflated via an inflation lumen that communicates with a source of pressurized fluid (not shown). Alternatively, a non-inflatable mechanism rather than a balloon could expand the conduit 202, or it could be in the form of a self-expanding stent that is retained in its collapsed orientation by a cover or sleeve. The conduit 202 preferably is covered during delivery into the left ventricle and the heart wall to prevent the elements 206 from damaging tissue. Thus, a sheath 212 is placed over the conduit 202 to cover some (and preferably most or all) of the elements 206.

The delivery device 204 may comprise an elongated shaft provided with a mechanism for securing the device to the guide wire 208 which extends through a heart chamber (such as left ventricle 12) and the wall of a coronary artery (such as LAD 30). The conduit 202 is moved into the heart chamber 12 and is placed in the heart wall 34, as shown in FIG. 18A. The position of the conduit 202 relative to the heart wall 34 and the LAD 30 can be controlled and adjusted as explained above.

The conduit 202 is preferably positioned in the sheath 212 so that a portion 214 including end 216 extends beyond the sheath (FIG. 18A). This permits the portion 214 of the conduit 202 to be expanded to a larger size than the portion of the conduit within the sheath 212. As shown in FIG. 18B, the balloon 210 is inflated and expands the portion 216 of the conduit 202; however, the sheath 212 prevents or limits expansion of the remaining portion of the conduit.

After this step, the sheath 212 is removed from the conduit 202, for example, pulling an end 218 of the sheath through the opening in the wall 38 of the LAD 30, as shown in FIG. 18C. The sheath is preferably made of a strong yet soft, collapsible material that allows the sheath to be folded and removed through the small opening in the wall of the artery. The materials described above with respect to the sheath 180 of the previous embodiment may be used. The expanded portion 216 of the conduit 202 aids in retaining the conduit in the heart wall while the sheath is removed. The resulting configuration is shown in FIG. 18D.

Next, the balloon 210 is inflated to expand the entire conduit 202, as shown in FIG. 18E. The conduit expands along its remaining length (i.e., other than expanded portion 216) to the orientation shown in FIG. 18F. After the sheath 212 has been removed and the conduit 202 expanded, the stent elements 206 are forced against the tissue of the heart wall to retain the conduit in position. The expanded portion 216 provides an enlarged opening through which blood may flow from the left ventricle 12 into the LAD 30, and also serves to secure the conduit within the heart wall. When expanded to the orientation shown in FIG. 18E, the entire conduit is preferably, though not necessarily, in its maximum radial strength position.

The balloon 210 is then deflated and removed from the conduit 202, for example, by moving the delivery device 204 and balloon 210 into the left ventricle 12 and then out of the heart (with or without removing the guide wire 208). After this, the opening in the wall 38 of left ventricle 12 is repaired leaving the conduit 202 positioned as shown in FIG. 18F. As can be seen, the conduit 202 assumes a funnel shape by way of the sheath restricting expansion of a portion of the conduit; however, it will be appreciated that this shape may be obtained in an alternative manner.

It will be understood that the invention encompasses many variations of the preferred systems and methods described in detail herein. As an example, rather than, or in conjunction with, delivering a conduit into the heart wall, a guide member placed as described above may be used to deliver a tissue removal device into the chamber. The tissue removal device can be used to core a channel in the heart wall and/or remove a portion of the wall of the coronary vessel. If used in conjunction with placing a conduit in the heart wall, for example, in order to core a channel in the wall that receives the conduit, it should be recognized that the tissue removal device may be separate from or combined with the conduit delivery device. The device may instead be used to form a channel in the heart wall that remains open to provide a blood flow path without using a conduit.

Several suitable tissue removal devices that may be used with a guide member are disclosed in commonly owned, copending application, U.S. application Ser. No. 09/170, 994, filed on Oct. 13, 1998, and entitled "DELIVERING A CONDUIT INTO A HEART WALL TO PLACE A CORONARY VESSEL IN COMMUNICATION WITH A HEART CHAMBER AND REMOVING TISSUE FROM THE VESSEL OR HEART WALL TO FACILITATE SUCH COMMUNICATION," the subject matter of which is incorporated herein by reference.

Moreover, it will be understood that the surgical approach depicted in FIG. 1 is but one exemplary manner of accessing the heart in order to utilize the systems, devices and methods of the invention. The approach illustrated in FIG. 1, which can be characterized as minimally invasive in that a thoracotomy is used as opposed to a median sternotomy, may be desirable in some applications. However, those skilled in the art will recognize that other approaches may be used to access the heart in order to practice the invention.

For example, an open surgical procedure including a median sternotomy may be used, or a minimally invasive procedure utilizing one or more relatively small access openings or ports may be used. Endoscopes or thoracoscopes may be used for visualization if the procedure is truly minimally invasive. Additionally, rather than forming one or more incisions in the patient's chest wall, an endovascular approach may be used to guide various inventive devices to the heart through the patient's vascular system to the heart, for example, by introducing the devices into a peripheral vessel such as the femoral artery.

Further, the exemplary embodiments are described primarily in connection with their use in a beating heart procedure. Nevertheless, it will be recognized that the systems, devices and methods of the invention may be used in stopped-heart procedures utilizing cardiopulmonary bypass (CPB), or procedures during which the heart is intermittently stopped and started. As a result, the detailed description of preferred embodiments set forth in the drawing Figures and accompanying disclosure should not be construed as limiting the applications for which the invention may find utility. The preferred embodiments of the invention are described above in detail for the purpose of setting forth a complete disclosure and for sake of explanation and clarity. It will be readily understood that the scope of the invention defined by the appended claims will encompass numerous changes and modifications to the embodiments disclosed herein. As an example, a guide member or conduit delivery device may include radiopaque markers for monitoring their position. Also, a guide member or conduit placed according to the invention may be used to deliver any medical device, such as tissue removal devices, or any pharmaceutical substance, such as angiogenic growth factors or other substances that aid in the perfusion of surrounding myocardial tissue.

What is claimed is:

1. A system for placing a guide member through the wall of a patient's heart so that the guide member extends through a coronary vessel and the wall of the heart into a heart chamber, the system comprising:

an introducer sized and configured for placement through a coronary vessel and the wall of a patient's heart into a heart chamber;

a guide member sized and configured to be positioned in the introducer and placed through the coronary vessel and the heart wall into the heart chamber, the guide member having a proximal portion adapted to remain outside the heart and a distal portion adapted to be passed into and then back out of the heart chamber; and a device adapted to remove the guide member from the heart chamber;

wherein the guide member is passed through the introducer and moves through the coronary vessel and the heart wall to a location within the heart chamber.

2. The system of claim 1, wherein the introducer is a hollow sleeve, the guide member is a guide wire, and the distal portion of the guide wire includes a distal end that is passed through the introducer.

3. The system of claim 1, wherein the device is a snare adapted to grasp the guide member and pull the guide member out of the heart chamber.

4. The system of claim 1, wherein the distal portion of the guide member is configured to be carried out of the heart chamber by blood flowing out of the heart chamber.

5. The system of claim 4, wherein the distal portion of the guide member supports a balloon that is engaged by blood flowing out of the heart chamber.

6. The system of claim 5, wherein the guide member comprises a guide wire coupled to a catheter supporting the balloon, and the balloon pulls the catheter and the guide wire into the heart chamber.

7. A system for placing a guide member through the wall of a patient's heart so that the guide member extends through a coronary vessel and the wall of the heart into a heart chamber, the system comprising:

an introducer sized and configured for placement through the coronary vessel and wall of a patient's heart into a heart chamber;

a guide member sized and configured to be passed through the coronary vessel and the heart wall into the heart chamber, the guide member having a proximal portion adapted to remain outside the heart and a distal portion adapted to be passed into the heart chamber; and a device adapted to remove the guide member from the heart chamber;

wherein one of the introducer and the guide member is configured to direct the distal portion of the guide member to a predetermined location within the heart chamber upon introducing the guide member into the chamber.

8. A system for delivering a conduit into the wall of a patient's heart to communicate a coronary vessel with a heart chamber, the system comprising:

an introducer configured for placement through the heart wall and into a heart chamber;

a guide member sized and configured to be positioned in the introducer and placed through the heart wall into the heart chamber, wherein the guide member is a guide wire; and a conduit sized and configured for placement in the wall of the heart so as to communicate the heart chamber with a coronary vessel, the conduit configured to be coupled to the guide wire for delivery into the heart chamber and placement in the wall of the heart;

wherein the conduit is supported by a delivery device having a clamp for being locked to the guide wire to allow the guide wire to be detachably coupled to the conduit.

9. A system for delivering a conduit into the wall of a patient's heart to communicate a coronary vessel with a heart chamber, the system comprising:

an introducer configured for placement through the heart wall and into a heart chamber;

a guide member sized and configured to be positioned in the introducer and placed through the heart wall into the heart chamber;

a conduit sized and configured for placement in the wall of the heart so as to communicate the heart chamber with coronary vessel, the conduit configured to be coupled to the guide member for delivery into the heart chamber and placement in the wall if the heart; and a device for removing the guide member from the heart chamber.

10. The system of claim 9, wherein the guide member is a guide wire.

11. The system of claim 10, wherein the guide member is coupled to the conduit by a detachable coupling mechanism.

12. The system of claim 11, wherein the conduit is supported by a delivery device that is coupled to the guide wire.

13. The system of claim 12, wherein the delivery device has a clamp for locking the delivery device to the guide wire.

14. The system of claim 12, wherein the delivery device has a support removably disposed within the conduit.

15. A method for placing a guide member in a patient's heart so that the guide member extends through a coronary vessel and the wall of the heart into a heart chamber containing blood, the method comprising steps of:

(a) passing a first end of a guide member through the coronary vessel and through the wall of the heart so that the guide member passes into the heart chamber containing blood;

(b) maintaining a second end of the guide member outside the heart chamber; and (c) passing the first end of the guide member back out of the heart chamber.

16. The method of claim 15, wherein step (a) is carried out by passing a first end of the guide member through the vessel and the heart wall into the heart chamber and then passing the first end of the guide member back out of the heart chamber, wherein the first end of the guide member is then used to deliver a conduit.

17. The method of claim 16, wherein the first end of the guide member is passed through an opening in the heart wall and removed from the heart chamber.

18. The method of claim 17, further comprising introducing a snare through the heart wall into the heart chamber and grasping the guide member to remove the first end of the guide member from the heart chamber.

19. The method of claim 15, wherein the first end of the guide member is configured to be forced out of the heart chamber by blood flow to pull the guide member out of the heart chamber.

20. The method of claim 19, wherein the heart chamber is the left ventricle and the first end of the guide member is forced into the aorta by blood flow and is then removed from the aorta.

21. The method of claim 15, further comprising using the guide member to deliver a tissue removal device into the heart chamber for use in removing tissue from the heart wall.

22. A method for placing a conduit in the wall of a patient's heart to establish a blood flow path between a coronary vessel and a heart chamber, the method comprising steps of:
- (a) positioning a guide member that extends through the coronary vessel and the heart wall into a heart chamber;
- (b) using the guide member to deliver a conduit into the heart chamber; and
- (c) positioning the conduit in the heart wall to establish a blood flow path between the heart chamber and the interior of the vessel;
- wherein step (a) is carried out by passing a first end of the guide member through the vessel and the heart wall into the heart chamber and then passing the first end of the guide member back out of the heart chamber, wherein the first end of the guide member is then used to deliver the conduit.

23. The method of claim 22, wherein step (b) is carried out by coupling the conduit to the first end of the guide member and then moving the first end of the guide member and the conduit into the heart chamber.

24. The method of claim 23, wherein step (a) is carried out while maintaining a second end of the guide member outside the heart, and further comprising pulling the second end of the guide member to move the first end of the guide member and the conduit into the heart chamber.

25. The method of claim 22, wherein step (b) is carried out by sliding the conduit over the first end of the guide member and then along the guide member into the heart chamber.

26. The method of claim 22, further comprising removing the guide member from the heart chamber after the conduit has been positioned in the heart wall.

27. The method of claim 22, wherein the conduit comprises a stent movable between collapsed and expanded orientations, and step (c) is carried out by placing at least a portion of the stent in the heart wall and then moving the stent to its expanded orientation.

28. The method of claim 22, wherein the conduit is covered by a sheath, and further comprising covering at least a portion of the conduit while placing the conduit in the heart wall and then removing the sheath.

29. The method of claim 22, wherein the coronary vessel is a coronary artery and the heart chamber is the left ventricle.

30. The method of claim 29, wherein the conduit is positioned in the heart wall so that the conduit extends into the lumen of the coronary artery and the interior of the left ventricle.

31. A method for placing a conduit in the wall of a patient's heart to establish a blood flow path between a coronary vessel and a heart chamber, the method comprising steps of:
- (a) positioning a guide member that extends through the coronary vessel and the heart wall into a heart chamber;
- (b) using the guide member to deliver a conduit into the heart chamber; and
- (c) positioning the conduit in the heart wall to establish a blood flow path between the heart chamber and the interior of the vessel;
- wherein the conduit is covered by a sheath, and further comprising covering at least a portion of the conduit while placing the conduit in the heart wall and then removing the sheath.

* * * * *